US008927452B2

(12) United States Patent
Hagemeyer et al.

(10) Patent No.: US 8,927,452 B2
(45) Date of Patent: Jan. 6, 2015

(54) METHOD FOR PRODUCING A SHELL CATALYST AND CORRESPONDING SHELL CATALYST

(75) Inventors: Alfred Hagemeyer, Bad Aibling (DE); Gerhard Mestl, München (DE); Peter Scheck, Gilching (DE); Sybille Ungar, München (DE)

(73) Assignee: SUD-Chemie AG, Munich (DE)

( * ) Notice: Subject to any disclaimer, the term of this patent is extended or adjusted under 35 U.S.C. 154(b) by 0 days.

(21) Appl. No.: 12/601,777

(22) PCT Filed: May 30, 2008

(86) PCT No.: PCT/EP2008/004328
§ 371 (c)(1),
(2), (4) Date: Apr. 21, 2010

(87) PCT Pub. No.: WO2008/145388
PCT Pub. Date: Dec. 4, 2008

(65) Prior Publication Data
US 2010/0197488 A1   Aug. 5, 2010

(30) Foreign Application Priority Data
May 31, 2007   (DE) .......................... 10 2007 025 442

(51) Int. Cl.
*B01J 21/00*   (2006.01)
*B01J 23/00*   (2006.01)
(Continued)

(52) U.S. Cl.
CPC ............ *B01J 35/008* (2013.01); *C07C 67/055* (2013.01); *B01J 37/0221* (2013.01); *B01J 23/66* (2013.01); *B01J 2/16* (2013.01)
USPC ........... 502/100; 502/300; 502/325; 502/337; 502/345; 427/213

(58) Field of Classification Search
USPC .......................... 502/232–355, 100; 427/213
See application file for complete search history.

(56) References Cited

U.S. PATENT DOCUMENTS

| 2,656,323 A | 10/1953 | Bielawski et al. |
| 3,252,757 A | 5/1966 | Granquist |

(Continued)

FOREIGN PATENT DOCUMENTS

| CA | 1267880 | 4/1990 |
| CA | 1267882 | 4/1990 |

(Continued)

OTHER PUBLICATIONS

IN248153, Huttlin et al., Published Jun. 24, 2011, English language equivalent of WO2006/027009.*

(Continued)

*Primary Examiner* — Anthony J Zimmer
(74) *Attorney, Agent, or Firm* — RatnerPrestia

(57) ABSTRACT

The present invention relates to a method for producing a shell catalyst which comprises a porous shaped catalyst support body with an outer shell in which at least one catalytically active species is present. In order to provide a shell catalyst production method by means of which shell catalysts can be produced, said shell catalysts having, over a comparatively large region of their shell thickness, a substantially uniform concentration of catalytically active species and having a substantially uniform shell thickness, what is proposed is a method using an device which is designed to generate, by means of a process gas, a fluid bed of shaped catalyst support bodies in which the shaped catalyst support bodies circulate elliptically or toroidally, preferably toroidally, comprising the steps of charging the device with shaped catalyst support bodies and generating a shaped catalyst support body fluid bed by means of a process gas, the shaped catalyst support bodies circulating elliptically or toroidally in the fluid bed, preferably toroidally; impregnating an outer shell of the shaped catalyst support body with a catalytically active species or precursor thereof by spraying the shaped catalyst support bodies circulating elliptically or toroidally in the fluid bed with a solution comprising a catalytically active species or a precursor thereof; drying the shaped catalyst support bodies sprayed with the solution.

24 Claims, 6 Drawing Sheets

(51) Int. Cl.
*B01J 25/00* (2006.01)
*B01J 29/00* (2006.01)
*H01M 4/88* (2006.01)
*B01J 23/70* (2006.01)
*B01J 23/72* (2006.01)
*B05D 7/00* (2006.01)
*B01J 35/00* (2006.01)
*C07C 67/055* (2006.01)
*B01J 37/02* (2006.01)
*B01J 2/16* (2006.01)
*B01J 23/66* (2006.01)

(56) References Cited

U.S. PATENT DOCUMENTS

| | | |
|---|---|---|
| 3,259,589 A | 7/1966 | Michalko |
| 3,565,919 A * | 2/1971 | Friedrichsen ............ 549/249 |
| 3,617,489 A | 11/1971 | Csicsery |
| 3,962,135 A | 6/1976 | Alafandi |
| 4,155,730 A | 5/1979 | Biberbach et al. |
| 4,407,733 A | 10/1983 | Birkenstock et al. |
| 4,409,410 A | 10/1983 | Cosyns et al. |
| 4,521,618 A * | 6/1985 | Arntz et al. ............ 562/535 |
| 4,621,072 A * | 11/1986 | Arntz et al. ............ 502/178 |
| 4,844,790 A | 7/1989 | Occelli |
| 4,970,804 A | 11/1990 | Hüttlin |
| 4,977,126 A * | 12/1990 | Mauldin et al. ........... 502/242 |
| 4,990,266 A | 2/1991 | Vorlop et al. |
| 5,015,453 A | 5/1991 | Chapman |
| 5,066,365 A | 11/1991 | Roscher et al. |
| 5,145,650 A | 9/1992 | Hüttlin |
| 5,175,136 A | 12/1992 | Felthouse |
| 5,179,056 A | 1/1993 | Bartley |
| 5,189,123 A | 2/1993 | Gropper et al. |
| 5,213,771 A | 5/1993 | Hilliard et al. |
| 5,248,644 A | 9/1993 | Johnson |
| 5,250,487 A | 10/1993 | Wirtz et al. |
| 5,304,525 A | 4/1994 | Immel et al. |
| 5,369,069 A | 11/1994 | Suzuki |
| 5,422,329 A | 6/1995 | Wirtz et al. |
| 5,559,071 A * | 9/1996 | Abel et al. ............ 502/326 |
| 5,567,839 A | 10/1996 | Gulliver et al. |
| 5,571,771 A | 11/1996 | Abel et al. |
| 5,591,688 A | 1/1997 | Blum et al. |
| 5,622,908 A | 4/1997 | Abel et al. |
| 5,648,576 A | 7/1997 | Nguyen Than et al. |
| 5,650,371 A | 7/1997 | Culross |
| 5,665,667 A | 9/1997 | Lemanski et al. |
| 5,668,074 A | 9/1997 | Wu et al. |
| 5,700,753 A | 12/1997 | Wang et al. |
| 5,753,583 A | 5/1998 | Heineke et al. |
| 5,801,285 A | 9/1998 | Waldmann et al. |
| 5,808,136 A | 9/1998 | Tacke et al. |
| 5,888,472 A | 3/1999 | Bem et al. |
| 5,935,889 A | 8/1999 | Murrell et al. |
| 5,990,344 A | 11/1999 | Couves et al. |
| 6,015,769 A | 1/2000 | Wang |
| 6,017,847 A | 1/2000 | Wang |
| 6,074,979 A * | 6/2000 | Hagemeyer et al. ........... 502/159 |
| 6,090,746 A | 7/2000 | Bönnemann et al. |
| 6,156,927 A | 12/2000 | Halcom et al. |
| 6,207,610 B1 | 3/2001 | Krause et al. |
| 6,228,800 B1 | 5/2001 | Yamaguchi et al. |
| 6,268,522 B1 | 7/2001 | Hagemeyer et al. |
| 6,288,295 B1 | 9/2001 | Didillon |
| 6,313,063 B1 | 11/2001 | Rytter et al. |
| 6,316,383 B1 | 11/2001 | Tacke et al. |
| 6,350,717 B1 | 2/2002 | Frenzel et al. |
| 6,350,900 B1 | 2/2002 | Wang et al. |
| 6,358,882 B1 | 3/2002 | Salem et al. |
| 6,367,165 B1 | 4/2002 | Hüttlin |
| 6,395,676 B2 | 5/2002 | Blum et al. |
| 6,399,813 B1 | 6/2002 | Blum et al. |
| 6,420,308 B1 | 7/2002 | Khanmamedova |
| 6,486,093 B2 | 11/2002 | Wang et al. |
| 6,492,299 B1 | 12/2002 | Couves et al. |
| 6,528,453 B2 | 3/2003 | Baker et al. |
| 6,528,683 B1 * | 3/2003 | Heidemann et al. ........... 562/542 |
| 6,534,438 B1 | 3/2003 | Baker et al. |
| 6,534,672 B2 | 3/2003 | Salem et al. |
| 6,593,270 B1 | 7/2003 | Krause et al. |
| 6,603,038 B1 | 8/2003 | Hagemeyer et al. |
| 6,605,739 B1 | 8/2003 | Karim et al. |
| 6,734,131 B2 | 5/2004 | Shih et al. |
| 6,797,669 B2 | 9/2004 | Zhang et al. |
| 6,806,382 B2 | 10/2004 | Baker et al. |
| 6,821,922 B1 | 11/2004 | Tacke et al. |
| 6,849,243 B1 | 2/2005 | Hagemeyer et al. |
| 6,898,869 B2 | 5/2005 | Hüttlin |
| 6,949,141 B2 | 9/2005 | Hüttlin |
| 6,987,200 B2 | 1/2006 | Hagemeyer et al. |
| 6,992,040 B2 | 1/2006 | Müller et al. |
| 7,288,686 B2 | 10/2007 | Ryu |
| 7,468,455 B2 | 12/2008 | Mazanec et al. |
| 7,569,508 B2 | 8/2009 | Zhou et al. |
| 7,797,854 B2 | 9/2010 | Huettlin |
| 8,207,327 B2 | 6/2012 | Laar et al. |
| 2001/0018401 A1 | 8/2001 | Blum et al. |
| 2001/0048970 A1 | 12/2001 | Hagemeyer et al. |
| 2002/0028966 A1 | 3/2002 | Blum et al. |
| 2002/0052290 A1 | 5/2002 | Bowman et al. |
| 2002/0062039 A1 | 5/2002 | Salem et al. |
| 2003/0003035 A1 | 1/2003 | Stamires et al. |
| 2003/0036476 A1 | 2/2003 | Arnold et al. |
| 2003/0047586 A1 | 3/2003 | Shibasaki et al. |
| 2003/0144544 A1 | 7/2003 | Baker et al. |
| 2003/0187293 A1 | 10/2003 | Birke et al. |
| 2003/0187294 A1 * | 10/2003 | Hagemeyer et al. ........... 560/241 |
| 2003/0195114 A1 | 10/2003 | Tacke et al. |
| 2003/0233012 A1 | 12/2003 | Jackson et al. |
| 2004/0048937 A1 * | 3/2004 | Srinivasan et al. ............ 518/726 |
| 2004/0235650 A1 | 11/2004 | Saleh et al. ............ 502/258 |
| 2005/0034322 A1 * | 2/2005 | Huttlin ............ 34/588 |
| 2005/0181940 A1 * | 8/2005 | Wang et al. ............ 502/330 |
| 2005/0203320 A1 | 9/2005 | Ryu |
| 2006/0035780 A1 | 2/2006 | Xu |
| 2006/0135809 A1 * | 6/2006 | Kimmich et al. ............ 560/241 |
| 2006/0266673 A1 * | 11/2006 | Rende et al. ............ 208/120.1 |
| 2007/0041795 A1 | 2/2007 | Neto et al. |
| 2007/0135302 A1 * | 6/2007 | Neto et al. ............ 502/300 |
| 2007/0191651 A1 | 8/2007 | Coupard et al. |
| 2007/0234586 A1 * | 10/2007 | Huettlin ............ 34/77 |
| 2008/0287290 A1 | 11/2008 | Wang et al. |
| 2009/0305882 A1 | 12/2009 | Dahar |
| 2010/0140181 A1 | 6/2010 | Tastayre |
| 2010/0185010 A1 | 7/2010 | Hagemeyer |
| 2010/0222209 A1 | 9/2010 | Kashani-Shirazi |
| 2011/0017289 A1 | 1/2011 | Park |
| 2011/0166010 A1 | 7/2011 | Hagemeyer et al. |
| 2012/0279556 A1 | 11/2012 | Choi |

FOREIGN PATENT DOCUMENTS

| | | |
|---|---|---|
| CA | 1268018 | 4/1990 |
| CA | 1268165 | 4/1990 |
| CA | 2 338 961 A1 | 2/2000 |
| CA | 2612435 | 12/2006 |
| CN | 1929916 | 3/2007 |
| DE | 1 286 021 | 1/1969 |
| DE | 27 03 801 A1 | 8/1978 |
| DE | 28 48 978 A1 | 5/1980 |
| DE | 29 45 913 A1 | 6/1981 |
| DE | 31 19 850 A1 | 2/1982 |
| DE | 261 104 A5 | 10/1988 |
| DE | 40 06 935 A1 | 12/1991 |
| DE | 40 39 026 A1 | 6/1992 |
| DE | 44 05 876 A1 | 10/1995 |
| DE | 44 43 705 A1 | 6/1996 |
| DE | 19534493 | 3/1997 |
| DE | 195 38 799 A1 | 4/1997 |
| DE | 196 01 861 A1 | 7/1997 |
| DE | 19734974 A1 | 2/1999 |
| DE | 197 34 975 A1 | 3/1999 |

(56) References Cited

FOREIGN PATENT DOCUMENTS

| | | |
|---|---|---|
| DE | 198 34 569 A1 | 2/2000 |
| DE | 199 04 147 A1 | 8/2000 |
| DE | 199 14 066 A1 | 10/2000 |
| DE | 100 64 084 A1 | 7/2002 |
| DE | 697 11 320 T2 | 7/2002 |
| DE | 102 48 116 B3 | 4/2004 |
| DE | 20 2005 003 791 U1 | 7/2006 |
| DE | 602 06 752 T2 | 7/2006 |
| DE | 10 2005 029 200 A1 | 12/2006 |
| DE | 102007025223 | 12/2008 |
| DE | 102007025443 | 12/2008 |
| EP | 0 064 301 A1 | 11/1982 |
| EP | 0262962 | 4/1988 |
| EP | 0 370 167 A1 | 5/1990 |
| EP | 0 436 787 B1 | 7/1991 |
| EP | 0 565 952 A1 | 10/1993 |
| EP | 0 634 208 A1 | 1/1995 |
| EP | 0 634 209 A1 | 1/1995 |
| EP | 0 634 214 A1 | 1/1995 |
| EP | 0 723 810 A1 | 7/1996 |
| EP | 0 839 793 A1 | 5/1998 |
| EP | 0 839 797 A1 | 5/1998 |
| EP | 0 882 507 A1 | 12/1998 |
| EP | 0 899 013 A1 | 3/1999 |
| EP | 1 102 635 | 2/2000 |
| EP | 1 323 469 A2 | 7/2003 |
| EP | 1 452 230 A1 | 9/2004 |
| EP | 1 979 073 | 7/2007 |
| GB | 585571 | 2/1947 |
| GB | 1 258 371 | 1/1970 |
| GB | 1 229 749 | 4/1971 |
| GB | 1 283 737 | 8/1972 |
| JP | 0648724 | 2/1994 |
| JP | 2003-527962 | 9/2003 |
| JP | 2005246197 | 9/2005 |
| JP | 2006-239588 | 9/2006 |
| JP | 2006-255600 | 9/2006 |
| JP | 2007-506540 | 3/2007 |
| JP | 2011501691 | 1/2011 |
| KR | 19960000019 | 1/1996 |
| KR | 1020060103514 | 10/2006 |
| KR | 1020110047714 | 5/2011 |
| WO | WO 98/14274 A1 | 4/1998 |
| WO | WO 98/18553 | 5/1998 |
| WO | WO 98/37102 | 8/1998 |
| WO | WO 99/22860 | 5/1999 |
| WO | WO 99/62632 | 12/1999 |
| WO | WO 00/58008 | 10/2000 |
| WO | WO 02/100527 | 12/2002 |
| WO | WO 2005/061107 | 7/2005 |
| WO | WO 2005/065821 A1 | 7/2005 |
| WO | WO 2006/027009 A1 | 3/2006 |
| WO | WO 2006/045606 A1 | 5/2006 |
| WO | WO 2006/078926 A1 | 7/2006 |
| WO | WO 2008/107050 A1 | 9/2008 |

OTHER PUBLICATIONS

International Search Report PCT/EP2008/004328 dated Oct. 9, 2008.
PCT International Preliminary Report on Patentability for PCT EP2008/004328 dated Feb. 2, 2010.
Office Action in U.S. Appl. No. 12/601,399 dated May 9, 2012.
Response filed in U.S. Appl. No. 12/601,399 on Aug. 9, 2012.
Office Action in U.S. Appl. No. 12/601,419 dated Jan. 30, 2012.
Response filed in U.S. Appl. No. 12/601,419 on May 30, 2012.
Office Action in U.S. Appl. No. 12/601,419 dated Aug. 6, 2012.
Response filed in U.S. Appl. No. 12/601,419 on Oct. 5, 2012.
Office Action in U.S. Appl. No. 12/601,420 dated Jun. 18, 2012.
Response filed in U.S. Appl. No. 12/601,420 on Oct. 18, 2012.
Office Action in U.S. Appl. No. 12/602,315 dated Aug. 16, 2012.
Office Action in U.S. Appl. No. 12/601,900 dated Jan. 4, 2012.
Office Action in U.S. Appl. No. 12/601,985 dated Feb. 7, 2013.
Kohl et al., Gas purification, 5$^{th}$ Edition, Gulf Publishing Company pp. 40-73 (1997).
Komai et al., Journal of Catalysis 120, 370-376 (1989).
L.A. Boot et al., Journal of Material Science, vol. 31, 1996, pp. 3115-3121 (1996).
Lehrbuch de anorganischen Chemie, Hollemann Wiberg, de Gruyter 102, Auflage, (ISBN 978-3-11-017770-1), pp. 955-970, term Schichtsllkate (2007).
Reddy et al., Fluor's Econamine FG Plus$^{SM}$ Technology, presented at the Second National Conference on Carbon Sequestration, National Energy Technology Department of Energy, Alexandria, VA, USE, pp. 1-11, May 5-8, 2003.
Usubharatana et al., Energy Procedia, vol. 1, Issue 1, pp. 95-102 (2009).
Elliott P. Barrett et al., "The Determination of Pore Volume and Area Distributions in Porous Substances. I. Computations from Nitrogen Isotherms," *J. Am. Chem. Soc.*, vol. 73, 1951, pp. 373-380.
Stephen Brunauer et al., "Adsorption of Gases in Multimolecular Layers," *J. Am. Chem. Soc.*, vol. 60, 1938, pp. 309-319.
Textbook of Inorganic Chemistry, Hollemann Wiberg, de Gruyter, 102$^{nd}$ Edition, 2007 (ISBN 978-3-11-017770-1), at pp. 955-959, 965-970.
Römpp Chemical Dictionary, 10$^{th}$ Edition, Georg Thieme Verlag, at pp. 374-375, 1997.
Römpp Chemical Dictionary, 10$^{th}$ Edition, Georg Thieme Verlag, at pp. 3427-3428, 1997.
Montrnorillonite, Mineral Data Publishing, Version 1.2 (2001).
Figueroa, Hyperfine Study on Sol-gel Derived-Hematite Doped zirconia, Chem. Mater., 2005, 17:3486-3491.
International Search Report of PCT/EP2008/004335 mailed Dec. 2, 2008.
Response filed in U.S. Appl. No. 12/601,420 on Nov. 14, 2013.
Chinese Serach Report for Application No. 200980147978.8 dated Jun. 2013.
International Search Report of PCT/EP2008/004327 mailed Jan. 28, 2009.
International Search Report of PCT/EP2008/004329 mailed Feb. 27, 2009.
International Search Report of PCT/EP2009/008469 filed Nov. 27, 2009, mailed Apr. 28, 2010.
Notice of Allowance in U.S. Appl. No. 12/601,399 dated Feb. 26, 2013.
Office Action in U.S. Appl. No. 12/601,399 dated Dec. 19, 2012.
Office Action in U.S. Appl. No. 12/601,419 dated Dec. 20, 2012.
Office Action in U.S. Appl. No. 12/602,315 dated Jan. 17, 2013.
Office Action in U.S. Appl. No. 13/129,915 mailed May 29, 2014.
Office Action in U.S. Appl. No. 13/129,915 mailed Oct. 16, 2013.
Response filed in U.S. Appl. No. 12/601,399 on Feb. 18, 2013.
Response filed in U.S. Appl. No. 12/601,419 on Apr. 22, 2013.
Response filed in U.S. Appl. No. 12/601,419 on Jun. 25, 2013.
Response filed in U.S. Appl. No. 12/601,419 on Jul. 18, 2013.
Response filed in U.S. Appl. No. 12/601,985 dated Jun. 7, 2013.
Response filed in U.S. Appl. No. 12/602,315 on Apr. 17, 2013.
Response filed in U.S. Appl. No. 12/602,315 on Nov. 12, 2012.
Response filed in U.S. Appl. No. 13/129,915 dated Apr. 16, 2014.
Stauffer, D. et al., Introduction to Percolation Theory, 2nd Edition, Taylor and Fransis, London, 1994.
International Search Report of PCT/EP2008/004334 mailed Aug. 29, 2008.
International Search Report of PCT/EP2008/004332 mailed Mar. 5, 2009.
International Search Report of PCT/EP2008/004333 mailed Nov. 26, 2008.
Office Action in U.S. Appl. No. 12/602,315 mailed Apr. 2, 2014.
Response filed in U.S. Appl. No. 12/601,777 on Feb. 27, 2014.
Response filed in U.S. Appl. No. 12/601,399 on Oct. 25, 2012.
Office Action in U.S. Appl. No. 12/601,419 dated Aug. 2, 2013.
Office Action in U.S. Appl. No. 12/601,420 dated Aug. 14, 2013.
Office Action in U.S. Appl. No. 12/601,985 dated Sep. 24, 2013.
Notice of Allowance in U.S. Appl. No. 12/601,419 dated Sep. 24, 2013.

\* cited by examiner

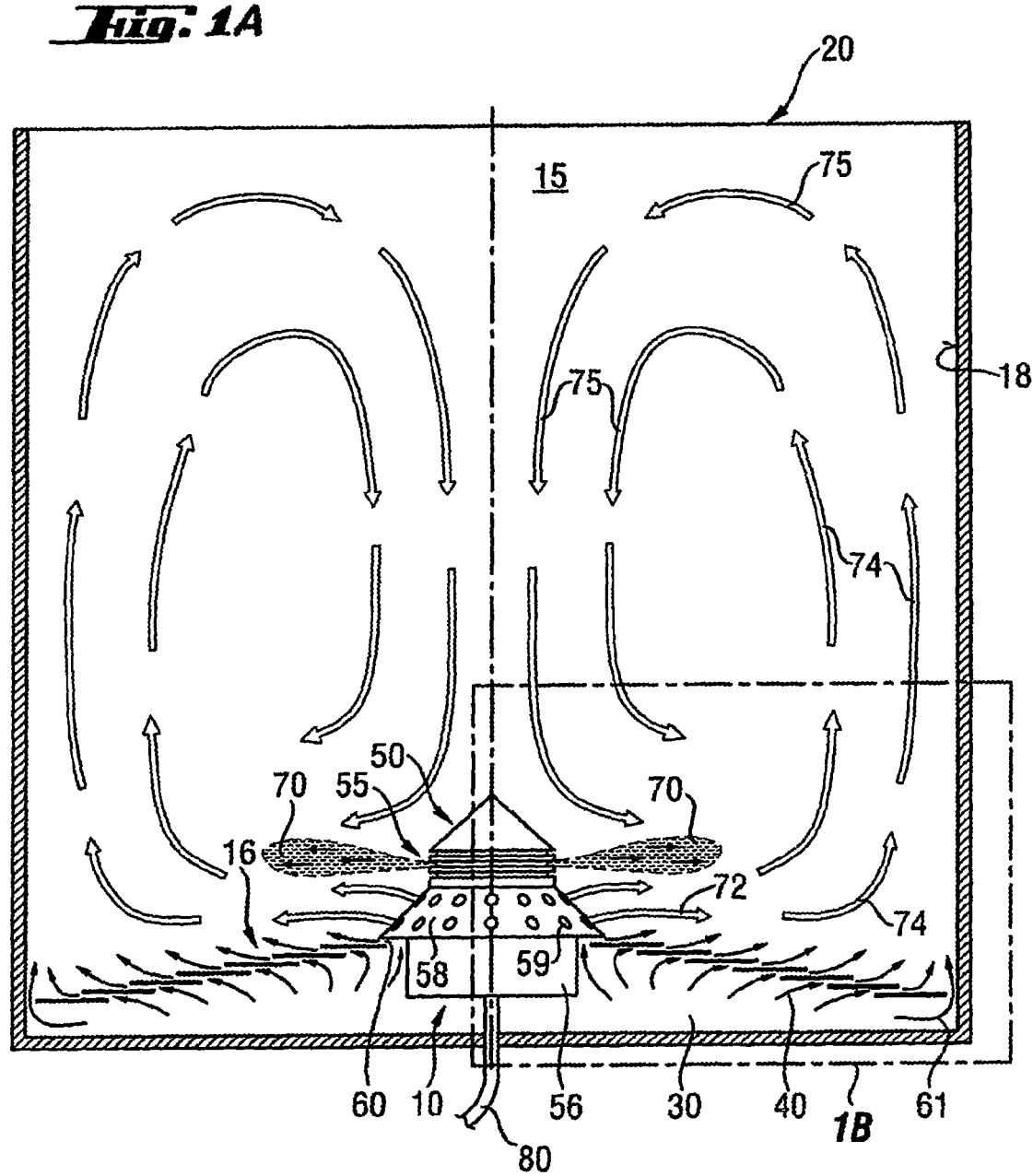

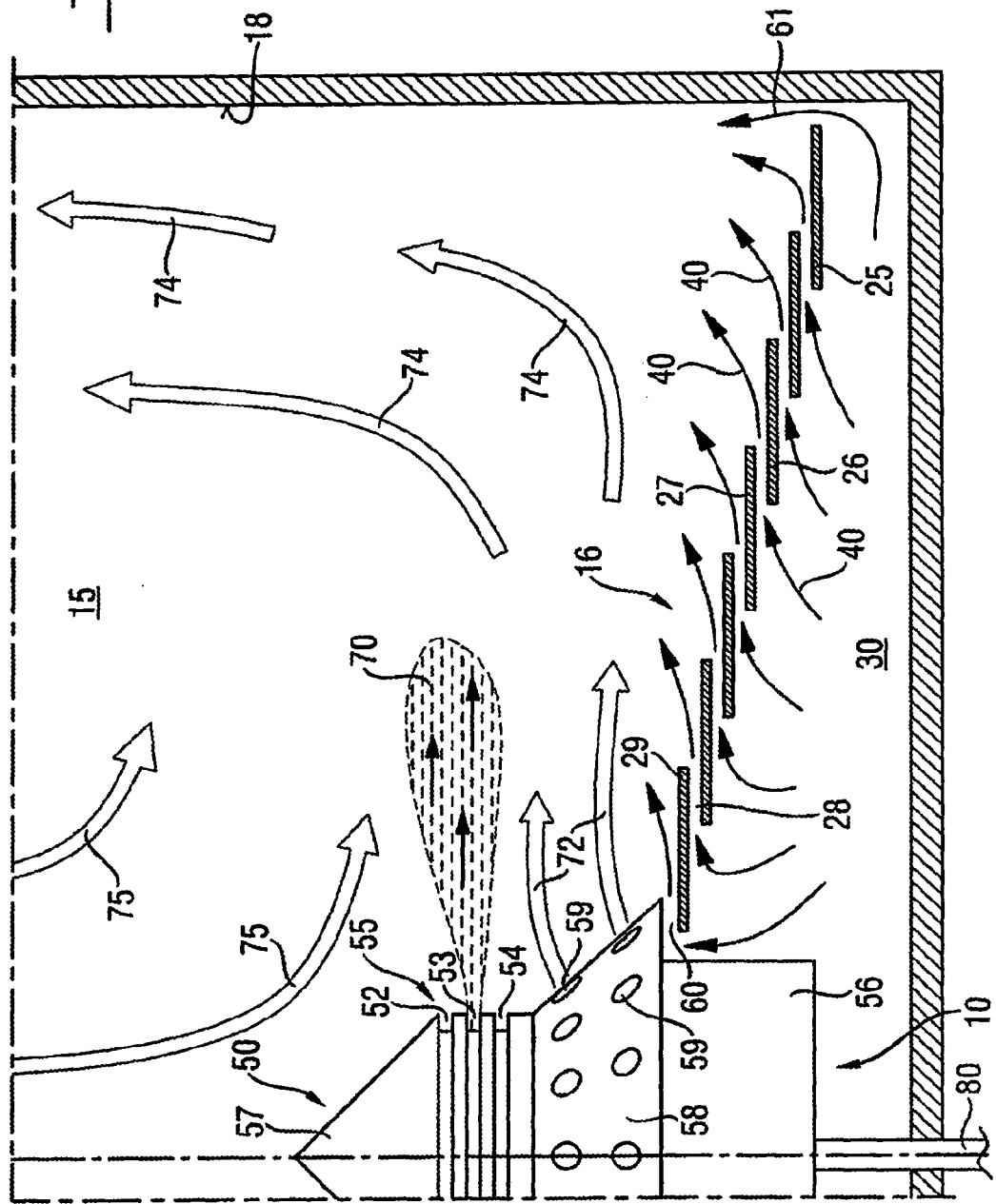

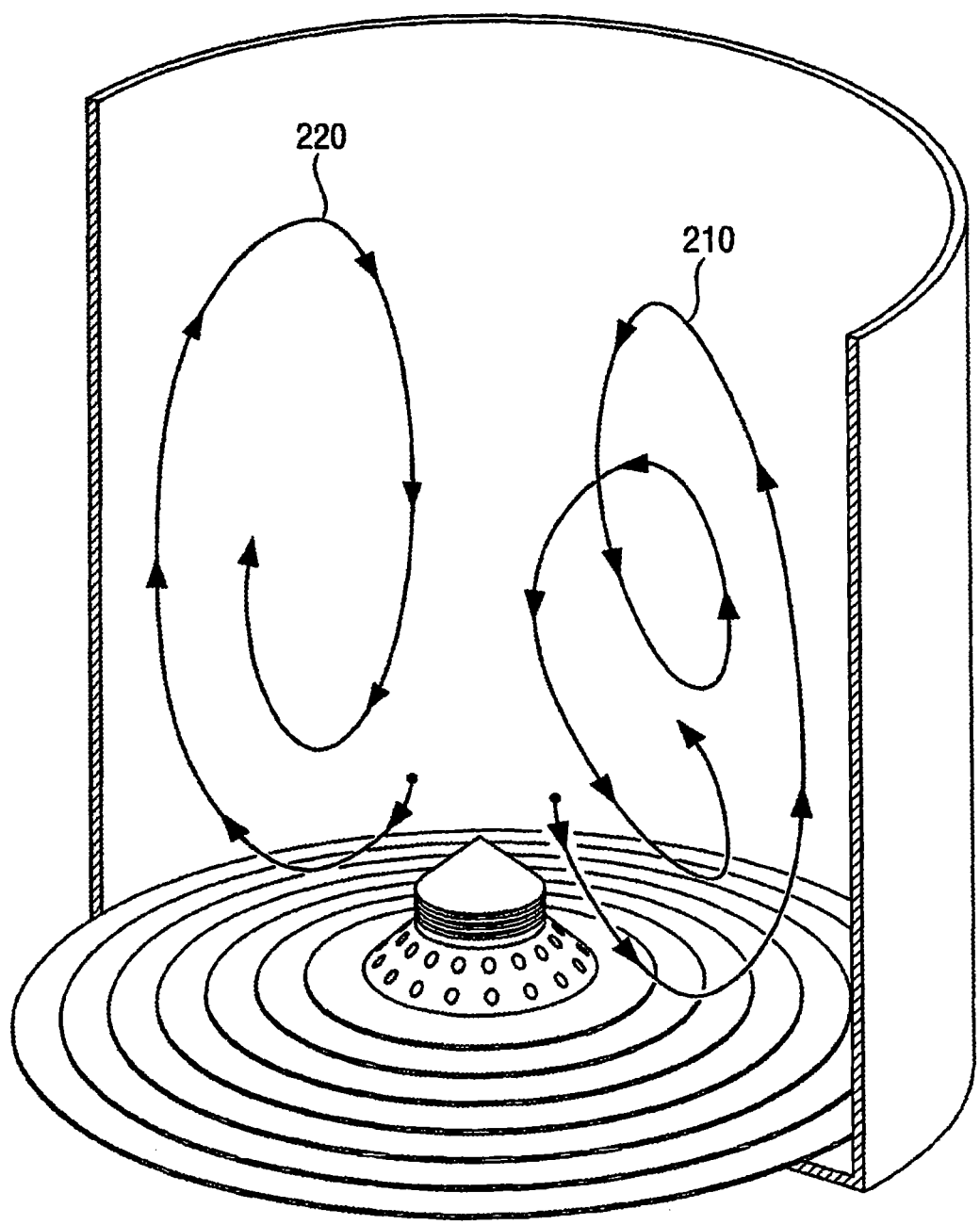

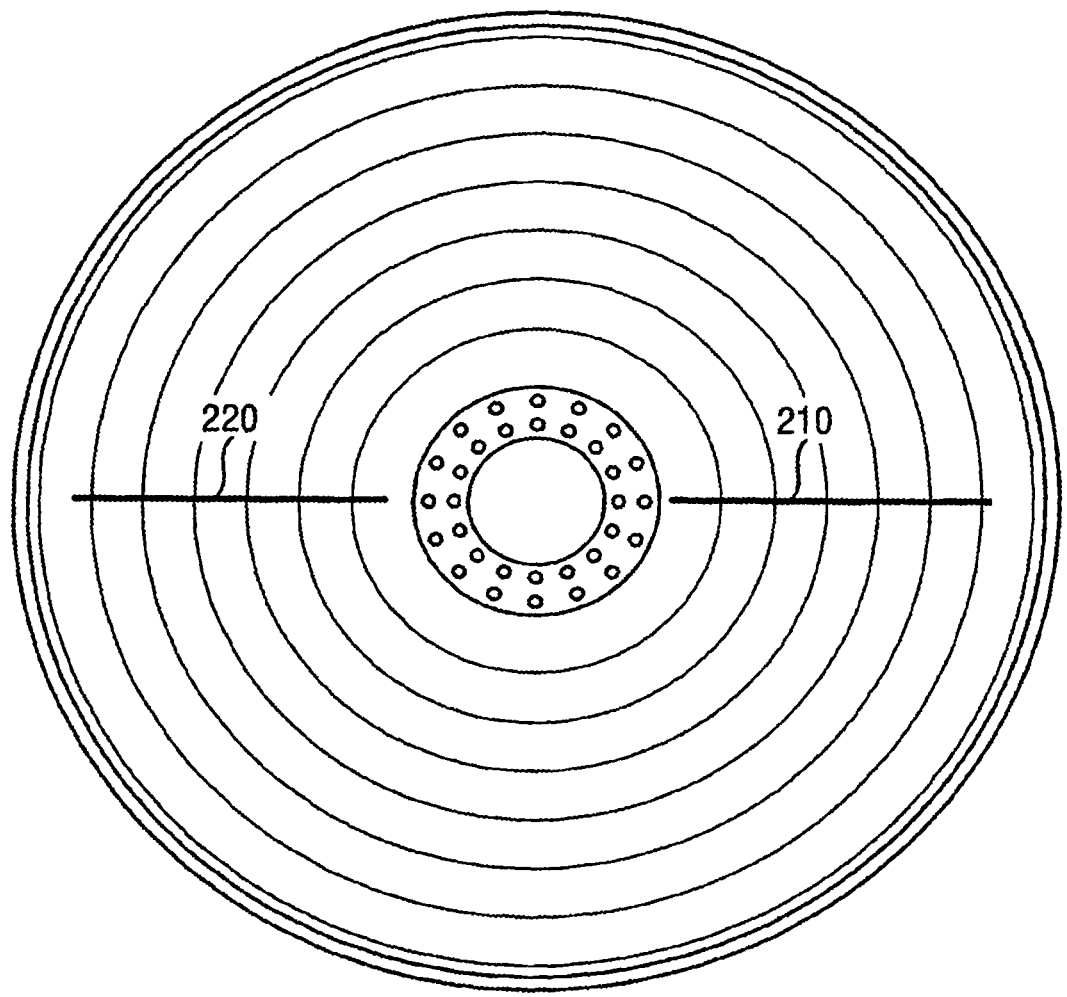

METHOD FOR PRODUCING A SHELL CATALYST AND CORRESPONDING SHELL CATALYST

CROSS REFERENCE TO RELATED APPLICATIONS

This application is a U.S. National Phase Application of PCT International Application PCT/2008/004328, filed May 30, 2008, which claims priority to German Application DE 102007025442.5, filed May 31, 2007, the contents of both applications being incorporated by reference herein for all purposes.

FIELD OF THE INVENTION

The present invention relates to a method for producing a shell catalyst which comprises a porous catalyst support shaped body with an outer shell in which at least one catalytically active species is present.

DESCRIPTION OF RELATED ART

Shell catalysts and processes for the preparation thereof are known in the prior art. In shell catalysts, the catalytically active species—and frequently also the promoters—are present only in a more or less broad outer region (shell) of a shaped catalyst support body, i.e. they do not completely penetrate the shaped catalyst support body (cf., for example, EP 565 952 A1, EP 634 214 A1, EP 634 209 A1 and EP 634 208 A1). With shell catalysts, a more selective reaction is possible in many cases than with catalysts in which the support is laden with the catalytically active species right into the support core ("through-impregnated").

Vinyl acetate monomer (VAM), for example, is currently prepared in high selectivity predominantly by means of shell catalysts. The majority of the currently used shell catalysts for preparing VAM are shell catalysts with a Pd/Au shell on a porous, amorphous aluminosilicate support configured as a sphere and based on natural sheet silicates which have been through-impregnated with potassium acetate as a promoter. In the Pd/Au system of these catalysts, the active metals Pd and Au are presumably not present in the form of metal particles of the particular pure metal, but rather in the form of Pd/Au alloy particles of possibly different composition, although the presence of unalloyed particles cannot be ruled out.

The VAM shell catalysts are typically produced by a so-called chemical route in which the catalyst support is impregnated with solutions or appropriate metal compounds, for example by immersing the support into the solutions, or by means of the incipient wetness method (pore filling method), in which the support is laden with a volume of a solution corresponding to its pore volume.

The Pd/Au shell of a VAM shell catalyst is obtained, for example, by first impregnating the shaped catalyst support bodies with an $Na_2PdCl_4$ solution in a first step and then fixing the Pd component with NaOH solution onto the catalyst support in the form of a palladium hydroxide compound in a second step. In a subsequent separate third step, the catalyst support is then impregnated with an $NaAuCl_4$ solution and then the Au component is likewise fixed by means of NaOH. It is, for example, also possible to impregnate the support first with alkali and then to apply the precursor compounds to the support thus pretreated. After the noble metal components have been fixed on the catalyst support, the laden catalyst support is then washed to very substantially free it of chloride and sodium ions, then dried, and finally reduced with ethylene at 150° C. The Pd/Au shell obtained typically has a thickness of from about 100 to 500 μm, and the thinner the thickness of the shell of a shell catalyst, the higher the product selectivity generally is.

Typically, after the fixing or reduction step, the catalyst support loaded with the noble metals is then loaded with potassium acetate. The loading with potassium acetate is effected not only in the outer shell loaded with noble metals, but rather the catalyst support is instead through-impregnated completely with the promoter.

According to the prior art, the active metals Pd and Au are applied thereon by means of impregnation in the region of a shell of the support proceeding from chloride compounds. However, this technique has reached its limits as far as the minimum shell thicknesses and maximum Au loading are concerned. The thinnest achievable shell thickness of correspondingly produced VAM catalysts is in the best case approx. 100 μm and it is not foreseeable that even thinner shells can be obtained by means of impregnation. Furthermore, the catalysts produced by means of impregnation have nonuniform shell thicknesses and a very nonuniform concentration of catalytically active species over comparatively large regions of their shell thickness, which can have an adverse effect on the product selectivity and on the activity of the catalyst.

SUMMARY OF THE INVENTION

It is therefore an object of the present invention to provide a shell catalyst production method by means of which it is possible to produce shell catalysts which, over comparatively large regions of their shell thickness, have a substantially uniform concentration of catalytically active species and a substantially uniform shell thickness.

This object is achieved by a method using an device which is designed to generate, by means of a process gas, a fluid bed of shaped catalyst support bodies in which the shaped catalyst support bodies circulate elliptically or toroidally, preferably toroidally, said method comprising the following steps
  a) charging the device (10) with shaped catalyst support bodies and generating a shaped catalyst support body fluid bed by means of a process gas (40), the shaped catalyst support bodies circulating elliptically or toroidally in the fluid bed, preferably toroidally;
  b) impregnating an outer shell of the shaped catalyst support body with a catalytically active species or precursor thereof by spraying the shaped catalyst support bodies circulating elliptically or toroidally in the fluid bed with a solution comprising a catalytically active species or a precursor thereof;
  c) drying the shaped catalyst support bodies sprayed with the solution.

It has been found that, surprisingly, by means of the method according to the invention, it is possible to produce shell catalysts which, over large regions of their shell thickness, have a substantially uniform concentration of catalytically active species and a substantially uniform shell thickness. Furthermore, it is possible by means of the method according to the invention to produce catalysts with very thin shells, for example less than 100 μm.

Furthermore, the shell catalysts produced by means of the method according to the invention, compared to catalysts produced by means of methods known from the prior art, feature an increased activity.

If the shell catalyst is to contain a plurality of different catalytically active species in the shell, for example a plurality of active metals or one active metal and one promoter metal, the shaped catalyst support body can be subjected correspondingly frequently to the method according to the invention. Alternatively, the method according to the invention can also be carried out with mixed solutions which comprise the desired different catalytically active species or precursors thereof. In addition, in the method according to the invention, the catalyst supports can be sprayed simultaneously with different solutions of different catalytically active species or precursors thereof.

By means of the method according to the invention, it is possible to produce shell catalysts whose concentration of catalytically active species, over a region of 90% of the shell thickness, the region being spaced apart from the outer and inner shell limit in each case by 5% of the shell thickness, deviates from the mean concentration in this region of catalytically active species from +/−3 to not more than +/−20%.

Furthermore, the method according to the invention has the advantage that, by means of this method, charges comprising a multitude of shell catalysts can be produced, whose ratio of the standard deviation of their shell thickness relative to the mean of the shell thickness is less than/equal to 20%. Such values are not attained by means of the methods known in the prior art for producing shell catalysts.

The shaped bodies sprayed with the solution are dried, in the method according to the invention, preferably continuously by means of the process gas. However, a separate final drying step may also be carried out after impregnation with continuous drying. In the first case, for example, the temperature of the process gas and of the shaped bodies can be used to individually adjust the drying rate and hence the penetration depth (thickness of the shell); in the second case, drying can be effected by any drying method known to be suitable by the person skilled in the art.

Device for performing the method according to the invention is described, for example, in documents WO 2006/027009 A1, DE 102 48 116 B3, EP 0 370 167 A1, EP 0 436 787 B1, DE 199 04 147 A1, DE 20 2005 003 791 U1, whose contents are incorporated into the present application by reference.

Further suitable fluid bed systems which are preferred in accordance with the invention are sold by the companies Glatt GmbH (Binzen, Germany), Aeromatic-Fielder AG (Bubendorf, Switzerland), Fluid Air Inc. (Aurora, Ill., USA), Hüttlin GmbH (Steinen, Germany), Umang Pharmatech Pvt. Ltd. (Maharashtra, India) and Innojet Technologies (Lörrach, Germany). Fluid bed device which is particularly preferred for the performance of the method according to the invention is sold by Innojet Technologies under the names Innojet® Ventilus or Innojet® AirCoater. These devices include a cylindrical vessel with a fixed vessel base installed so as to be immobile, in the center of which is mounted a spray nozzle. The base consists of circular lamellae which are mounted in stages one above another. The process air flows between the individual lamellae horizontally and eccentrically with a circumferential flow component outward in the direction of the vessel wall into the vessel. This forms so-called sliding air layers on which the shaped catalyst support bodies are initially transported outward in the direction of the vessel wall. On the outside at the vessel wall is installed a vertically aligned process air stream which directs the catalyst supports upward. Having arrived at the top, the catalyst supports move on a tangential path in the direction of the center of the base, in the course of which they pass through the spray mist of the nozzle. After passing through the spray mist, the movement operation described begins anew. The process air control described provides the basis for a substantially homogeneous toroidal fluid bed-like circulating motion of the catalyst supports.

The interaction of the spraying with the fluid bed-like elliptical or toroidal circulating motion of the catalyst supports in the fluid bed has the effect, in contrast to a corresponding conventional fluid bed, that the individual catalyst supports pass through the spray nozzle with approximately equal frequency. Furthermore, the circulation operation also ensures that the individual catalyst supports carry out rotation about their own axis, which is why the catalyst supports are impregnated particularly uniformly.

In the method according to the invention, a fluid bed is generated, in which the shaped bodies circulate elliptically or toroidally. In the prior art, the transition of the particles of a bed into a state in which the particles are completely freely mobile (fluid bed) is referred to as the fluidization point, and the corresponding fluid velocity as the fluidization velocity. It is preferred in accordance with the invention that, in the method according to the invention, the fluid velocity is up to four times the fluidization velocity, preferably up to three times the fluidization velocity and more preferably up to twice the fluidization velocity.

In an alternative embodiment of the method according to the invention, the fluid velocity may be up to 1.4 times the common logarithm of the fluidization velocity, preferably up to 1.3 times the common logarithm of the fluidization velocity and more preferably up to 1.2 times the common logarithm of the fluidization velocity.

The terms "shaped catalyst support body", "catalyst support", "shaped body" and "support" are used synonymously in the context of the present invention.

In the method according to the invention, the shaped catalyst support bodies circulate elliptically or toroidally in the fluid bed, preferably toroidally. In order to give an impression of how the shaped bodies move in the fluid bed, it is stated that, in the case of "elliptical circulation", the shaped catalyst support bodies in the fluid bed move in a vertical plane on an elliptical path with varying size of the main and secondary axis. In the case of "toroidal circulation", the shaped catalyst support bodies move in the fluid bed in a vertical plane on an elliptical path with varying size of the main and secondary axis, and in a horizontal plane on a circular path with varying size of the radius. On average, the shaped bodies move, in the case of "elliptical circulation" in a vertical plane on an elliptical path, and, in the case of "toroidal circulation", on a toroidal path, i.e. a shaped body travels helically along the surface of a torus with a vertically elliptical section.

In the case that the method according to the invention is carried out by means of a solution of a precursor of a catalytically active species, the method further comprises a step of converting the precursor to the corresponding catalytically active species. The conversion of the precursor can be carried out with the aid of any method which is known to be suitable for the method according to the invention by the person skilled in the art.

To accomplish a shaped catalyst support body fluid bed in which the shaped catalyst support bodies circulate elliptically or toroidally in a manner which is simple from a process technology point of view and hence inexpensive, in accordance with a further preferred embodiment of the method according to the invention, the device comprises a process chamber with a bottom and a side wall, the process gas being introduced into the process chamber through the bottom of the process chamber, which is preferably constructed from a plurality of mutually overlapping annular guide plates laid one on top of another, between which annular slots are formed, with a horizontal movement component directed radially outward.

By virtue of the process gas being introduced into the process chamber with a horizontal movement component directed radially outward, elliptical circulation of the catalyst supports in the fluid bed is brought about. If the shaped bodies are to circulate toroidally in the fluid bed, a circumferential movement component must additionally be imparted to the shaped bodies, which forces the shaped bodies onto a circular path. This circumferential movement component can be imparted to the shaped bodies, for example, by arranging appropriately directed guide paths on the side wall to deflect the catalyst supports. In a further preferred embodiment of the method according to the invention, however, a circumferential flow component is imparted to the process gas introduced into the process chamber. As a result, the generation of the shaped catalyst support body fluid bed in which the shaped catalyst support bodies circulate toroidally is ensured in a simple manner from a process technology point of view.

In order to impart the circumferential flow component to the process gas introduced into the process chamber, in a preferred embodiment of the method according to the invention, correspondingly shaped and aligned process gas guide elements may be arranged between the annular guide plates. Alternatively or additionally, the circumferential flow component can be imparted to the process gas introduced into the process chamber by introducing additional process gas into the process chamber with a movement component directed obliquely upward through the bottom of the process chamber, preferably in the region of the side wall of the process chamber.

The spraying of the shaped catalyst support bodies circulating in the fluid bed with the solution can be carried out by means of an annular gap nozzle which sprays a spray cloud, in which case the plane of symmetry of the spray cloud preferably runs parallel to the plane of the equipment base. As a result of the 360° extent of the spray cloud, the shaped bodies which fall down in the centre can be sprayed particularly uniformly with the solution. The annular gap nozzle, i.e. the opening thereof, is preferably embedded completely in the fluid bed.

In a further preferred embodiment of the method according to the invention, the annular gap nozzle is arranged centrally in the bottom and the opening of the annular gap nozzle is embedded completely in the fluid bed. This ensures that the free path length of the droplets of the spray cloud until they hit a shaped body is comparatively short and, correspondingly, comparatively little time remains for the droplets to coalesce to larger droplets, which might counteract the formation of a substantially uniform shell thickness.

In a further preferred embodiment of the method according to the invention, a gas support cushion can be brought about on the underside of the spray cloud. The cushion on the base side keeps the base surface substantially free of sprayed solution, i.e. virtually all of the solution sprayed is introduced into the fluid bed of shaped bodies, such that barely any spray losses occur, which is of significance for reasons of cost especially with regard to expensive noble metals/metal compounds or enzymes.

In a further preferred embodiment of the method according to the invention, the catalyst support is of spherical configuration. This ensures uniform rotation of the support about its axis and, associated with this, uniform impregnation of the catalyst support with the solution of the catalytically active species.

The catalyst supports used in the method according to the invention may be all porous shaped catalyst support bodies which can be circulated elliptically or toroidally by means of a process gas, and the supports can be formed from all materials or material mixtures. Preference is given in accordance with the invention, however, to those catalyst supports which comprise at least one metal oxide or are formed from such a metal oxide or a mixture thereof. The catalyst support preferably comprises a silicon oxide, an aluminum oxide, an aluminosilicate, a zirconium oxide, a titanium oxide, a niobium oxide or a natural sheet silicate, preferably a calcined acid-treated bentonite.

The term "natural sheet silicate", for which the term "phyllosilicate" is also used in the literature, is understood to mean untreated or treated silicate mineral originating from natural sources, in which $SiO_4$ tetrahedra which form the structural base unit of all silicates are crosslinked to one another in layers of the general formula $[Si_2O_5]^{2-}$. These tetrahedral layers form alternate layers with so-called octahedral layers in which a cation, in particular Al and Mg, is surrounded octahedrally by OH or O. For example, two-layer phyllosilicates and three-layer phyllosilicates are distinguished. Sheet silicates preferred in the context of the present invention are clay minerals, especially kaolinite, bidellite, hectorite, saponite, nontronite, mica, vermiculite and smectites, particular preference being given to smectites and especially to montmorillonite. Definitions of the term "sheet silicates" can be found, for example, in "Lehrbuch der anorganischen Chemie" [Textbook of inorganic chemistry], Hollemann Wiberg, de Gruyter, 102nd edition, 2007 (ISBN 978-3-11-017770-1) or in "Römpp Lexikon Chemie" [Römpp chemistry lexicon], 10th edition, Georg Thieme Verlag under the term "phyllosilicate". Typical treatments to which a natural sheet silicate is subjected before use as a support material include, for example, a treatment with acids and/or a calcination. A natural sheet silicate particularly preferred in the context of the present invention is a bentonite. Bentonites are not natural sheet silicates in the actual sense, but rather a mixture of predominantly clay minerals in which sheet silicates are present. In other words, in the present case, if the natural sheet silicate is a bentonite, this should be understood to mean that the natural sheet silicate is present in the catalyst support in the form of or as a constituent of a bentonite.

A catalyst support configured as a shaped body and based on natural sheet silicates, especially based on an acid-treated calcined bentonite, can be produced, for example, by shaping an acid-treated (uncalcined) bentonite as a shaping mixture comprising sheet silicate and water with compaction to a shaped body by means of device familiar to those skilled in the art, for example extruders or tableting presses, and then calcining the unhardened shaped body to a stable shaped body. The size of the specific surface area of the catalyst support depends especially on the quality of the (crude) bentonite used, on the acid treatment process of the bentonite used, i.e. for example, on the nature and on the amount relative to the bentonite, and on the concentration of the inorganic acid used, on the duration and the temperature of the acid treatment, on the compression pressure, and on the duration and temperature of the calcination, and also on the calcination atmosphere.

Acid-treated bentonites can be obtained by treatment of bentonites with strong acids, for example sulfuric acid, phosphoric acid or hydrochloric acid. A definition of the term "bentonite" which is also valid in the context of the present invention is given in Römpp, Lexikon Chemie, 10th ed., Georg Thieme Verlag. Bentonites particularly preferred in the context of the present invention are natural aluminum-containing sheet silicates which comprise montmorillonite (as a smectite) as the main mineral. After the acid treatment, the bentonite is generally washed with water, dried and ground to a powder.

It has been found that, by means of the method according to the invention, it is also possible to achieve comparatively high shell thicknesses. Indeed, the smaller the surface area of the support, the greater the achievable thickness of the shell. In a further preferred embodiment of the method according to the invention, the catalyst support may have a surface area of less than/equal to 160 $m^2/g$, preferably one of less than 140 $m^2/g$, preferentially one of less than 135 $m^2/g$, further preferably one of less than 120 $m^2/g$, more preferably one of less than 100 $m^2/g$, even more preferably one of less than 80 $m^2/g$ and especially preferably one of less than 65 $m^2/g$. In the context of the present invention, the term "surface area" of the catalyst support is understood to mean the BET surface area of the support, which is determined by means of adsorption of nitrogen to DIN 66132.

In a further preferred embodiment of the method according to the invention, the catalyst support has a surface area of from 160 to 40 $m^2/g$, preferably one of between 140 and 50 $m^2/g$, preferentially one of between 135 and 50 $m^2/g$, further preferably one of between 120 and 50 $m^2/g$, more preferably one of between 100 and 50 $m^2/g$, and most preferably one of between 100 and 60 $m^2/g$.

When the supports are circulated in the method according to the invention, the catalyst supports are stressed mechanically, which can result in a certain degree of attrition and a certain degree of damage to catalyst supports, especially in the region of the shell which forms. Especially in order to keep the attrition of the catalyst support within acceptable limits, the catalyst support has a hardness of greater than/equal to 20 N, preferably one of greater than/equal to 30 N, further preferably one of greater than/equal to 40 N and most preferably one of greater than/equal to 50 N. The determination of the hardness is determined by means of an 8M tablet hardness tester from Dr. Schleuniger Pharmatron AG on 99 shaped bodies as an average after drying at 130° C. for 2 h, the instrument settings being as follows:

Hardness: N
Distance from the shaped body: 5.00 mm
Time delay: 0.80 s
Advance type: 6 D
Speed: 0.60 mm/s The hardness of the catalyst support can be influenced, for example, by means of varying certain parameters in the method for its production, for example through the selection of the support material, the calcination time and/or the calcination temperature of an unhardened shaped body shaped from a corresponding support mixture, or through particular additives, for example methylcellulose or magnesium stearate.

For reasons of cost, the process gas used in the method according to the invention is preferably air. Should, however, for example, the catalytically active species or the precursor thereof react with atmospheric oxygen to give undesired compounds, the process gas used may also be an inert gas, for example nitrogen, methane, short-chain saturated hydrocarbons, one of the noble gases, preferably helium, neon or argon, or a halogenated hydrocarbon or a mixture of two or more of the above.

In a further preferred embodiment of the method according to the invention, the process gas, in particular in the case of expensive gases, for example helium, argon, etc., can be recycled into the device in a closed circuit.

In a further preferred embodiment of the method according to the invention, the catalyst support is heated before and/or during the application of the solution, for example by means of a heated process gas. The degree of heating of the catalyst supports can be used to determine the drying rate of the solution of the catalytically active species applied. At relatively low temperatures, for example, the drying rate is comparatively low, such that there may be formation of relatively great shell thicknesses in the case of corresponding quantitative application owing to the high diffusion of the active species or of the precursor thereof caused by the presence of solvent. At relatively high temperatures, for example, the drying rate is comparatively high, such that solution coming into contact with the catalyst support dries almost immediately, which is why solution applied on the catalyst support cannot penetrate deep into it. At comparatively high temperatures, shells with relatively small thicknesses and high loading of active species can thus be obtained. Accordingly, in a further preferred embodiment of the method according to the invention, the process gas is heated, preferably to a temperature of greater than/equal to 40° C., preferentially to a temperature of greater than/equal to 60° C., further preferably to a temperature of greater than/equal to 70° C. and most preferably to a temperature of from 60 to 100° C.

In order to prevent premature drying of droplets of the spray cloud, in a further preferred embodiment of the method according to the invention, the process gas, before being introduced into the device, may be enriched with the solvent of the solution, preferably within a range of from 10 to 50% of the saturation vapor pressure (at process temperature).

In a further preferred embodiment of the method according to the invention, the solvent added to the process gas and solvent from the drying of the shaped bodies can be removed from the process gas by means of suitable cooler units, condensers and separators, and recycled into the solvent enricher by means of a pump.

It may be preferred that the solution of the catalytically active species is the solution of a biocatalyst, preferably the solution of an enzyme. Especially enzyme solutions can be processed in a rapid and simple manner to give shell catalysts by means of the method according to the invention.

It is also possible to use solutions of metal compounds of any metals in the method according to the invention. However, it is preferred when the solution is a solution of a metal compound of a metal selected from the group consisting of the transition metals, especially the noble metals.

In addition, in a further preferred embodiment of the method according to the invention, the metal compounds may be selected from the halides, especially chlorides, oxides, nitrates, nitrites, formates, propionates, oxalates, acetates, hydroxides, hydrogencarbonates, amine complexes or organic complexes, for example triphenylphosphine complexes or acetylacetonate complexes, of the metals mentioned.

To produce a shell catalyst for oxidation reactions, in a further preferred embodiment of the method according to the invention, the solution is a solution of a Pd precursor compound.

To produce a silver-containing shell catalyst, in a further preferred embodiment of the method according to the invention, the solution of the catalytically active species or of a precursor thereof is a solution of an Ag compound.

To produce a platinum-containing shell catalyst, in a further preferred embodiment of the method according to the invention, the solution is a solution of a Pt precursor compound.

To produce a gold-containing shell catalyst, in a further preferred embodiment of the method according to the invention, the solution of the catalytically active species or of a precursor thereof is a solution of an Au compound.

Accordingly, to produce a nickel-, cobalt- or copper-containing shell catalyst, in a further preferred embodiment of the method according to the invention, the solution of the catalytically active species or of a precursor thereof may be a solution of a nickel, cobalt or copper compound.

In the methods described in the prior art for producing VAM shell catalysts based on Pd and Au, commercially available solutions of the precursor compounds, such as $Na_2PdCl_4$, $NaAuCl_4$ or $HAuCl_4$-solutions, are typically used. In recent literature, chloride-free Pd or Au precursor compounds, for example $Pd(NH_3)_4(OH)_2$, $Pd(NH_3)_2(NO_2)_2$ and $KAuO_2$, are also used. These precursor compounds are basic in solution, while the classic chloride, nitrate and acetate precursor compounds are all acidic in solution.

In principle, the Pd and Au precursor compound used may be any Pd or Au compound by means of which a high degree of dispersion of the metals can be achieved. The term "degree of dispersion" is understood to mean the ratio of the number of all surface metal atoms of all metal/alloy particles of a supported metal catalyst relative to the total number of all metal atoms of the metal/alloy particles. In general, it is preferred when the degree of dispersion corresponds to a comparatively high numerical value, since a maximum number of metal atoms are freely available for a catalytic reaction in this case. This means that, in the case of a comparatively high degree of dispersion of a supported metal catalyst, a particular catalytic activity thereof can be achieved with a comparatively small amount of metal used.

Examples of preferred Pd precursor compounds are water-soluble Pd salts. In a particularly preferred embodiment of the method according to the invention, the Pd precursor compound is selected from the group consisting of $Pd(NH_3)_4(OH)_2$, $Pd(NH_3)_4(OAc)_2$, $Pd(NH_3)_4(HCO_3)_2$, $Pd(NH_3)_4(HPO_4)$, $Pd(NH_3)_4Cl_2$, $Pd(NO_3)_2$, $K_2Pd(OAc)_2(OH)_2$, $Na_2Pd(OAc)_2(OH)_2$, $Pd(NH_3)_2(NO_2)_2$, $Pd(NH_3)_4(NO_3)_2$, $K_2Pd(NO_2)_4$, $Na_2Pd(NO_2)_4$, $Pd(OAc)_2$, $PdCl_2$, $H_2PdCl_4$, $(NH_4)_2PdCl_4$, $K_2PdCl_4$ and $Na_2PdCl_4$. In addition to $Pd(OAc)_2$, it is also possible to use other carboxylates of palladium, preferably the salts of the aliphatic monocarboxylic acids having from 3 to 5 carbon atoms, for example the propionate salt or the butyrate salt. Instead of $NH_3$, it is also possible to use the corresponding Pd compounds with ethylenediamine or ethanolamine as the ligand.

In a further preferred embodiment of the method according to the invention, palladium nitrite precursor compounds may also be preferred. Preferred palladium nitrite precursor compounds are, for example, those which are obtained by means of dissolution of $Pd(OAc)_2$ in an $NaNO_2$ solution.

Examples of preferred Au precursor compounds are water-soluble Au salts. In a particularly preferred embodiment of the method according to the invention, the Au precursor compound is selected from the group consisting of $KAuO_2$, $NaAuO_2$, $NMe_4AuO_2$, $KAuCl_4$, $(NH_4)AuCl_4$, $HAuCl_4$, $KAu(NO_2)_4$, $NaAu(NO_2)_4$, $AuCl_3$, $NaAuCl_4$, $KAu(OAc)_3(OH)$, $NaAu(OAc)_3(OH)$, $HAu(NO_3)_4$ and $Au(OAc)_3$. It may be advisable to make up the $Au(OAc)_3$ or the $KAuO_2$ freshly in each case by means of precipitation of the oxide/hydroxide from a gold acid solution, washing and isolating the precipitate, and taking it up into a acetic acid or KOH.

Examples of preferred Pt precursor compounds are water-soluble Pt salts. In a particularly preferred embodiment of the method according to the invention, the Pt precursor compound is selected from the group consisting of $Pt(NH_3)_4(OH)_2$, $K_2PtCl_4$, $K_2PtCl_6$, $Na_2PtCl_6$, $Pt(NH_3)_4Cl_2$, $Pt(NH_3)_4(HCO_3)_2$, $Pt(NH_3)_4(HPO_4)$, $Pt(NO_3)_2$, $K_2Pt(OAc)_2(OH)_2$, $Pt(NH_3)_2(NO_2)_2$, $PtCl_4$, $H_2Pt(OH)_6$, $Na_2Pt(OH)_6$, $K_2Pt(OH)_6$, $K_2Pt(NO_2)_4$, $Na_2Pt(NO_2)_4$, $Pt(OAc)_2$, $PtCl_2$ and $Na_2PtCl_4$. In addition to $Pt(OAc)_2$, it is also possible to use other carboxylates of platinum, preferably the salts of the aliphatic monocarboxylic acids having from 3 to 5 carbon atoms, for example the propionate salt or the butyrate salt.

In a further preferred embodiment of the method according to the invention, platinum nitrite precursor compounds may also be preferred. Preferred platinum nitrite precursor compounds are, for example, those which are obtained by dissolution of $Pt(OAc)_2$ in an $NaNO_2$ solution.

Examples of preferred Ag precursor compounds are water-soluble Ag salts. In a particularly preferred embodiment of the method according to the invention, the Ag precursor compound is selected from the group consisting of $Ag(NH_3)_2(OH)$, $Ag(NO_3)$, silver citrate, silver tartrate, ammonium silver oxalate, $K_2Ag(OAc)(OH)_2$, $Ag(NH_3)_2(NO_2)$, $Ag(NO_2)$, silver lactate, silver trifluoroacetate, silver oxalate, $Ag_2CO_3$, $K_2Ag(NO_2)_3$, $Na_2Ag(NO_2)_3$, $Ag(OAc)$, ammoniacal AgCl solution or ammoniacal $Ag_2CO_3$ solution or ammoniacal AgO solution. In addition to Ag(OAc), it is also possible to use other carboxylates of silver, preferably the salts of the aliphatic monocarboxylic acids having from 3 to 5 carbon atoms, for example the propionate salt or the butyrate salt. Instead of $NH_3$, it is also possible to use the corresponding ethylenediamines or other diamines of Ag.

In a further preferred embodiment of the method according to the invention, silver nitrite precursor compounds may also be preferred. Preferred silver nitrite precursor compounds are, for example, those which are obtained by means of dissolution of Ag(OAc) in an $NaNO_2$ solution.

The solvents used for metallic, catalytically active species or precursors thereof are all solvents in which the selected metal compound is soluble and which, after the application to the catalyst support, can be removed again readily therefrom by means of drying. Preferred solvents—examples of metal acetates as precursor compounds are in particular unsubstituted carboxylic acids, especially acetic acid, or ketones such as acetone, and, for the metal chlorides, in particular water or dilute hydrochloric acid.

If the precursor compound is insufficiently soluble in acetic acid, water or dilute hydrochloric acid or mixtures thereof, other solvents may also be used alternatively or additionally to the solvents mentioned. Useful other solvents here preferably include those solvents which are inert. Preferred solvents which are suitable as an additive to acetic acid include ketones, for example acetone or acetylacetone, and also ethers, for example tetrahydrofuran or dioxane, acetonitrile, dimethylformamide and solvents based on hydrocarbons, for example benzene.

Preferred solvents or additives which are suitable as an addition to water include ketones, for example acetone, or alcohols, for example ethanol or isopropanol or methoxyethanol, alkalis such as aqueous KOH or NaOH, or organic acids such as acetic acid, formic acid, citric acid, tartaric acid, malic acid, glyoxylic acid, glycolic acid, oxalic acid, pyruvic acid or lactic acid.

It is preferred when, in the method according to the invention, the solvent used in the method is recycled, preferably by means of suitable cooler units, condensers and separators.

In a further preferred embodiment of the method according to the invention, the shaped catalyst support body, after being sprayed with the solution of the catalytically active species or of a precursor thereof, is subjected to a fixing step to fix the catalytically active species or the precursor on the catalyst support. The fixing step may include, for example, with regard to noble metals, the treatment of the support with alkali, for example by spraying base onto the support in the device (fluid bed device) or by a calcination of the support to convert the metal components of the corresponding metal compounds to a hydroxide compound or to an oxide.

In the case of transition metal compounds which have been fixed on the catalyst support, for example, by means of a base, the support may subsequently be calcined to convert the metal component of the metal compound to the corresponding oxide form. After the loading with the precursor compounds or after the fixing of the metal components, the support may be calcined to convert the metal components to the corresponding oxides. The calcination is effected preferably at temperatures of less than 1000° C.

To produce supported transition metal or noble metal catalysts in the form of shell catalysts, the metal components are also reduced before the use of the catalyst, in which case the reduction can be carried out in situ, i.e. in the process reactor, or else ex situ, i.e. in a specific reduction reactor. The reduction in situ is preferably carried out with ethylene (5% by volume) in nitrogen at a temperature of about 150° C. over a period of, for example, 5 hours. The reduction ex situ can be carried out, for example, with 5% by volume of hydrogen in nitrogen, for example by means of forming gas, at temperatures in the range of preferably 150-500° C. over a period of 5 hours.

Gaseous or evaporable reducing agents, for example CO, $NH_3$, formaldehyde, methanol and hydrocarbons, can likewise be used, in which case the gaseous reducing agents may also be diluted with inert gas, for example carbon dioxide, nitrogen or argon. Preference is given to using a reducing agent diluted with inert gas. Preference is given to mixtures of hydrogen with nitrogen or argon, preferably having a hydrogen content between 1% by volume and 15% by volume.

The reduction of the transition metals or noble metals can also be undertaken in liquid phase, preferably by means of the reducing agents hydrazine, potassium formate, sodium formate, formic acid, $H_2O_2$, hypophosphorous acid or sodium hypophospite.

The amount of reducing agent is preferably selected such that, during the treatment time, at least the equivalent needed for complete reduction of the metal components is passed over the catalyst. Preference is given, however, to passing an excess of reducing agent over the catalyst in order to ensure a rapid and complete reduction.

Preference is given to reducing at ambient pressure, i.e. at an absolute pressure of approx. 1 bar. For the production of industrial amounts of inventive catalyst, preference is given to using a rotary tube oven, moving bed reactor or fluid bed reactor in order to ensure uniform reduction of the catalyst.

The present invention further relates to a shell catalyst comprising a porous shaped catalyst support body with an outer shell in which at least one catalytically active species is present, wherein the concentration of the catalytically active species, over a region of 90% of the shell thickness, the region being spaced apart from the outer and inner shell limit in each case by 5% of the shell thickness, deviates from the mean concentration of catalytically active species in this region by not more than +/−20%, preferably by not more than +/−15% and preferentially by not more than +/−10%. Such shell catalysts are obtainable by means of the method according to the invention.

When the catalytically active species and/or the promoter is a metal, its distribution in the support can be determined by producing a section of the catalyst, for example by halving the support. In the electron microscope, the three-dimensional distribution of the active metal or of the promoter metal can then be determined with the aid of WDX spectroscopy (wavelength-dispersive X-ray diffraction), which is also referred to as EDX spectroscopy (energy dispersive X-ray) In this case, a measurement head is conducted over the sample and is sensitive to the active metal, preferably palladium, or the promoter metal, preferably gold, such that the distribution thereof in the area can be determined.

By virtue of the substantially homogeneous distribution of the catalytically active species within the shell, a substantially uniform activity of the inventive catalyst over the thickness of the shell is ensured, since the concentration of active species over the shell thickness varies only comparatively little. In other words, the profile of the concentration of active species over the shell thickness describes approximately a rectangular function.

To further increase the selectivity of the inventive catalyst, viewed over the thickness of the shell of the catalyst, the maximum concentration of catalytically active species is in the region of the outer shell limit and the concentration declines in the direction of the inner shell limit. It may be preferred when the concentration of catalytically active species declines constantly over a region of at least 25% of the shell thickness in the direction of the inner shell limit, preferably over a region of at least 40% of the shell thickness and more preferably over a region of from 30 to 80% of the shell thickness.

In a further preferred embodiment of the inventive catalyst, the concentration of catalytically active species declines approximately constantly to a concentration of from 50 to 90% of the maximum concentration in the direction of the inner shell limit, preferably to a concentration of from 70 to 90% of the maximum concentration.

The invention further relates to a shell catalyst comprising a porous shaped catalyst support body and at least one catalytically active species which is present in an outer shell of the shaped catalyst support body, wherein the shell catalyst is one element of a charge of a multitude of shell catalysts, where the ratio of the standard deviation of the shell thicknesses of the shell catalysts of the charge relative to the mean value of the shell thicknesses of the shell catalysts of the charge is less than/equal to 20%, preferably less than/equal to 15%, preferentially less than/equal to 12% and more preferably less than/equal to 10%, or from 3 to 18%, preferably from 3 to 15%.

The standard deviation is determined according to the formula $$\sigma_X = \sqrt{\frac{1}{N-1}\sum_{i=1}^{N}(X_i - \overline{X})^2}$$

in which $\sigma_x$ is the standard deviation;

N(=100) is the sample size (number of shaped catalyst support bodies; N is equal to 100);

$X_i$ is the shell thickness on the i-th shaped catalyst support body of the sample;

$\overline{X}$ is the empirical mean value of the shell thickness of the sample (i.e. the arithmetic mean of the sample), which is determined according to the formula $$\overline{X} = \frac{1}{N} \sum_{i=1}^{N} X_i.$$

Such shell catalyst batches can be produced by means of the method according to the invention.

The catalytically active species may be a biocatalyst, preferably an enzyme. Alternatively, the inventive shell catalyst may comprise one metal or any combination of metals which are suitable as catalytically active metals or as a promoter metal. The metal may be present, for example, in metallic form, in ionic form or, for example, in complexed form. It is preferred when the metal is selected from the group of the transition metals, preferably from the group of the noble metals.

Catalysts preferred in accordance with the invention comprise two different metals in metallic form in the shell, the two metals being combinations of one of the following pairs: Pd and Ag; Pd and Au; Pd and Pt. Catalysts with a Pd/Au shell are suitable especially for producing VAM, those with a Pd/Pt shell are suitable especially as an oxidation and hydrogenation catalyst, and those with a Pd/Ag shell are suitable especially for the selective hydrogenation of alkynes and dienes in olefin streams, i.e. for example, for producing purified ethylene by selective hydrogenation of acetylene present in the crude product.

With regard to the provision of a VAM shell catalyst with sufficient VAM activity, it is preferred that the catalyst comprises, as the catalytically active species, Pd and Au, and the proportion in the catalyst of Pd is from 0.6 to 2.0% by mass, preferably from 0.7 to 1.8% by mass and preferentially from 0.8 to 1.5% by mass, based on the mass of the catalyst support laden with noble metal.

Furthermore, it is preferred in the aforementioned context that the Au/Pd atomic ratio of the catalyst is between 0 and 1.2, preferably between 0.1 and 1, preferentially between 0.3 and 0.9 and especially preferably between 0.4 and 0.8.

In the case of a Pd/Au shell catalyst, this catalyst preferably comprises, as a promoter, at least one alkali metal compound, preferably a potassium compound, a sodium compound, a cesium compound or a rubidium compound, preferably a potassium compound. The suitable and particularly preferred potassium compounds include potassium acetate KOAc, potassium carbonate $K_2CO_3$, potassium hydrogencarbonate $KHCO_3$ and potassium hydroxide KOH, and also all potassium compounds which can be converted under the particular reaction conditions of the VAM synthesis to potassium acetate KOAc. The potassium compound can be applied to the catalyst support either before or after the reduction of the metal components to the metals Pd and Au. In a further preferred embodiment of the inventive catalyst, the catalyst comprises an alkali metal acetate, preferably potassium acetate. To ensure a sufficient promoter activity, it is particularly preferred when the content in the catalyst of alkali metal acetate is from 0.1 to 0.7 mol/l, preferably from 0.3 to 0.5 mol/l.

In a further preferred embodiment of the inventive Pd/Au catalyst, the alkali metal/Pd atomic ratio is between 1 and 12, preferably between 2 and 10 and more preferably between 4 and 9. Preferably, the smaller the surface area of the catalyst support, the lower the alkali metal/Pd atomic ratio.

It has been found that the smaller the surface area of the catalyst support, the higher the product selectivities of the inventive Pd/Au catalyst. In addition, the smaller the surface area of the catalyst support, the greater the thickness of the metal shell that can be selected without having to accept significant losses of product selectivity. In a preferred embodiment of the inventive catalyst, the surface area of the catalyst support therefore has a surface area of less than/equal to 160 $m^2/g$, preferably one of less than 140 $m^2/g$, preferentially one of less than 135 $m^2/g$, further preferably one of less than 120 $m^2/g$, more preferably one of less than 100 $m^2/g$, even more preferably one of less than 80 $m^2/g$ and especially preferably one of less than 65 $m^2/g$.

In a further preferred embodiment of the inventive Pd/Au catalyst, the catalyst support may have a surface area of from 160 to 40 $m^2/g$, preferably one of between 140 and 50 $m^2/g$, preferentially one of between 135 and 50 $m^2/g$, further preferably one of between 120 and 50 $m^2/g$, more preferably one of between 100 and 50 $m^2/g$ and most preferably one of between 100 and 60 $m^2/g$.

With regard to a low pore diffusion limitation, in a further preferred embodiment of the inventive Pd/Au catalyst, the catalyst support may have a mean pore diameter of from 8 to 50 nm, preferably one of from 10 to 35 nm and preferentially one of from 11 to 30 nm.

The acidity of the catalyst support can advantageously affect the activity of the inventive catalyst. In a further preferred embodiment of the inventive catalyst, the catalyst support has an acidity of between 1 and 150 µeq/g, preferably one of between 5 and 130 µeq/g and more preferably one of between 10 and 100 µeq/g. The acidity of the catalyst support is determined as follows: 1 g of the finely ground catalyst support is admixed with 100 ml of water (with a pH blank value) and extracted with stirring for 15 minutes. Subsequently, the mixture is titrated with 0.01 N NaOH solution at least to pH 7.0, the titration being effected stepwise; first, 1 ml of the NaOH solution is added dropwise to the extract (1 drop/second), there is a wait of 2 minutes, the pH is read off, another 1 ml of NaOH is added dropwise, etc. The blank value of the water used is determined and the acidity calculation is corrected correspondingly.

The titration curve (ml of 0.01 NaOH against pH value) is then plotted and the point of intersection of the titration curve at pH 7 is determined. The molar equivalents are calculated in $10^{-6}$ equiv/g of support, which are found from the NaOH consumption for the point of intersection at pH 7.

$$\text{Total acid:} \quad \frac{10 * \text{ml } 0.01 \text{ N NaOH}}{1 \text{ support}} = \mu eq/g$$

The Pd/Au catalyst is preferably configured as a sphere. Accordingly, the catalyst support is configured as a sphere with a diameter of preferably greater than 1.5 mm, more preferably a diameter of greater than 3 mm and most preferably with a diameter of from 4 mm to 9 mm.

To increase the activity of the inventive Pd/Au catalyst, the catalyst support may be doped with at least one oxide of a metal selected from the group consisting of Zr, Hf, Ti, Nb, Ta, W, Mg, Re, Y and Fe, preferably with $ZrO_2$, $HfO_2$ or $Fe_2O_3$. It may be preferred when the proportion in the catalyst support of dopant oxide is between 0 and 20% by mass, preferably from 1.0 to 10% by mass and preferentially from 3 to 8% by mass, based on the mass of the catalyst support.

In an alternative embodiment of the inventive catalyst, it comprises, as the catalytically active species, Pd and Ag, and, in order to ensure a sufficient activity of the catalyst, preferably in the hydrogenation of acetylene, the proportion in the catalyst of Pd is from 0.01 to 1.0% by mass, preferably from 0.02 to 0.8% by mass and preferentially from 0.03 to 0.7% by mass, based on the mass of the catalyst support laden with noble metal.

Likewise in order to achieve a sufficient activity of the catalyst in the hydrogenation of acetylene, the Ag/Pd atomic ratio of the catalyst is between 0 and 10, preferably between 1 and 5, and it is preferred that the thickness of the noble metal shell is less than 60 μm.

In a further preferred embodiment of the inventive Pd/Ag catalyst, the catalyst support is configured as a sphere with a diameter of greater than 1.5 mm, preferably with a diameter of greater than 3 mm and preferentially with a diameter of from 2 to 5 mm, or as a cylindrical tablet with dimensions of up to 7×7 mm.

In a further preferred embodiment of the inventive Pd/Ag catalyst, the catalyst support has a surface area of from 1 to 50 $m^2/g$, preferably of between 3 and 20 $m^2/g$.

It may also be preferred that the catalyst support has a surface area of less than/equal to 10 $m^2/g$, preferably of less than 5 $m^2/g$ and preferentially of less than 2 $m^2/g$.

A preferred inventive oxidation or hydrogenation catalyst comprises, as the catalytically active species, Pd and Pt, the proportion in the catalyst of Pd to ensure a sufficient activity being from 0.05 to 5% by mass, preferably from 0.1 to 2.5% by mass and preferentially from 0.15 to 0.8% by mass, based on the mass of the catalyst support laden with noble metal.

In a preferred embodiment of the inventive Pd/Pt catalyst, the Pd/Pt atomic ratio of the catalyst is between 10 and 1, preferably between 8 and 5 and preferentially between 7 and 4.

In a further preferred embodiment of the inventive Pd/Pt catalyst, the catalyst support is configured as a cylinder, preferably with a diameter of from 0.75 to 3 mm and with a length of from 0.3 to 7 mm.

In addition, it may be preferred that the catalyst support has a surface area of from 50 to 400 $m^2/g$, preferably one of between 100 and 300 $m^2/g$.

It may also be preferred that the catalyst comprises, as the catalytically active species, metallic Co, Ni and/or Cu in the shell.

In a further preferred embodiment of the inventive catalyst, the catalyst support is a support based on a silicon oxide, an aluminum oxide, an aluminosilicate, a zirconium oxide, a titanium oxide, a niobium oxide or a natural sheet silicate, preferably a calcined acid-treated bentonite.

As already stated above, the catalyst support of the inventive catalyst is subject to a certain level of mechanical stress in the course of catalyst production. Furthermore, the inventive catalyst may be highly mechanically stressed when filled into a reactor, as a result of which there may be undesired evolution of dust and damage to the catalyst support, especially to its catalytically active shell disposed in an outer region. Especially in order to keep the attrition of the inventive catalyst within acceptable limits, the catalyst support has a hardness of greater than/equal to 20 N, preferably one of greater than/equal to 30 N, further preferably one of greater than/equal to 40 N and most preferably one of greater than/equal to 50 N. The pressure hardness is determined as described above.

The inventive catalyst may, as a catalyst support, preferably comprise a catalyst support based on a natural sheet silicate, especially on a calcined acid-treated bentonite. In the context of the present invention, the expression "based on" means that the catalyst comprises the corresponding material. According to the invention, it is preferred when the proportion in the catalyst support of the bentonite is greater than/equal to 50% by mass, preferably greater than/equal to 60% by mass, preferentially greater than/equal to 70% by mass, further preferably greater than/equal to 80% by mass, more preferably greater than/equal to 90% by mass and most preferably greater than/equal to 95% by mass, based on the mass of the catalyst support.

It has been found that the greater the integral pore volume of the catalyst support, the higher the product selectivity of the inventive Pd/Au catalyst. In a further preferred embodiment of the inventive catalyst, the catalyst support therefore has a BJH integral pore volume of greater than 0.30 ml/g, preferably one of greater than 0.35 ml/g and preferentially one of greater than 0.40 ml/g.

In addition, it may be preferred when the catalyst support of the Pd/Au catalyst has a BJH integral pore volume of between 0.3 and 1.2 ml/g, preferably one of between 0.4 and 1.1 ml/g and preferentially one of from 0.5 to 1.0 ml/g.

The integral pore volume of the catalyst support is determined by the BJH method by means of nitrogen adsorption. The surface area of the catalyst support and its integral pore volume are determined by the BET method and by the BJH method respectively. The BET surface area is determined by the BET method to DIN 66131; a publication of the BET method can also be found in J. Am. Chem. Soc. 60, 309 (1938). To determine the surface area and the integral pore volume of the catalyst support or of the catalyst, the sample can be analyzed, for example, with a fully automated ASAP 2010 nitrogen porosimeter from Micromeritics, by means of which an adsorption isotherm and desorption isotherm are recorded.

To determine the surface area and the porosity of the catalyst support or of the catalyst by the BET theory, the data are evaluated according to DIN 66131. The pore volume is determined from the measured data using the BJH method (E. P. Barret, L. G. Joiner, P. P. Haienda, J. Am. Chem. Soc. (73/1951, 373)). In this method, effects of capillary condensation are also taken into account. Pore volumes of particular pore size ranges are determined by summing incremental pore volumes which are obtained from the evaluation of the adsorption isotherm according to BJH. The integral pore volume according to the BJH method is based on pores having a diameter of from 1.7 to 300 nm.

In a further preferred embodiment of the inventive catalyst, the water absorption capacity of the catalyst support may be from 40 to 75%, preferably from 50 to 70%, calculated as the weight increase by water absorption. The absorption is determined by impregnating 10 g of the support sample with deionized water for 30 min until no further gas bubbles escape from the support sample. The excess water is then decanted and the impregnated sample is dabbed with a cotton towel to free the sample of adhering liquid. Subsequently, the water-laden support is weighed and the absorption is calculated according to:

(Final weight (g)−Starting weight (g))×10=Water absorption (%)

In a further preferred embodiment of the inventive catalyst, it may be preferred when at least 80% of the integral pore volume of the catalyst support is formed by mesopores and macropores, preferably at least 85% and preferentially at least 90%. This counteracts a reduced activity of the inventive catalyst brought about by diffusion limitation, especially in the case of shells with comparatively great thicknesses. In this context, the terms micropores, mesopores and macropores shall be understood, respectively, to mean pores which have a diameter of less than 2 nm, a diameter of from 2 to 50 nm and a diameter of greater than 50 nm.

The catalyst support of the inventive catalyst is configured as a shaped body. The catalyst support may in principle adopt the shape of any geometric figure on which a corresponding shell can be applied. However, it is preferred when the catalyst support is configured as a sphere, cylinder (including with rounded end faces), hollow cylinder (including with rounded end faces), trilobe, capped tablet, tetralobe, ring, donut, star, wagonwheel, inverse wagonwheel, or as an extrudate, preferably as a ribbed extrudate or star extrudate.

The diameter, i.e. the length and thickness, of the catalyst support of the inventive catalyst is preferably from 1 to 9 mm, according to the reactor tube geometry in which the catalyst is to be used.

In general, the lower the thickness of the shell of the catalyst, the higher the product selectivity of the inventive catalyst. In a further preferred embodiment of the inventive catalyst, the shell of the catalyst therefore has a thickness of less than 300 µm, preferably one of less than 200 µm, preferentially one of less than 150 µm, further preferably one of less than 100 µm and more preferably one of less than 80 µm. The thickness of the shell may, in the case of supported metal catalysts, frequently be measured optically by means of a microscope. The region in which the metals have been deposited appears black, while the metal-free regions appear white. The interface line between metal-containing and metal-free regions is generally very sharp and can clearly be recognized visually. Should the aforementioned interface line not be sharp and accordingly not clearly be recognizable visually or the shell thickness not be determinable visually for other reasons, the thickness of the shell corresponds to the thickness of a shell measured proceeding from the outer surface of the catalyst support in which 95% of the catalytically active species deposited on the support is present.

It has likewise been found that, in the inventive catalyst, the shell can be formed with a comparatively high thickness which brings about a high activity of the catalyst without bringing about a significant reduction in the product selectivity of the inventive catalyst. For this purpose, catalyst supports with a comparatively low surface area should be used. In another preferred embodiment of the inventive catalyst, the shell of the catalyst therefore has a thickness of between 200 and 2000 µm, preferably one of between 250 and 1800 µm, preferentially one of between 300 and 1500 µm and further preferably one of between 400 and 1200 µm.

The present invention further relates to the use of an device which is designed to generate, by means of a process gas, a fluid bed of shaped catalyst support bodies in which the shaped catalyst support bodies circulate elliptically or toroidally, preferably toroidally, to perform a method according to the invention or in the production of a shell catalyst, especially of an inventive shell catalyst. It has been found that, by means of such device, it is possible to produce shell catalysts which have the aforementioned advantageous properties.

In a preferred embodiment of the inventive use, the device comprises a process chamber with a bottom and a side wall, the bottom being constructed from a plurality of mutually overlapping annular guide plates laid one on top of another, between which annular slots are formed, through which the process gas can be introduced with an essentially horizontal movement component directed radially outward. This enables, in a simple manner from a process technology point of view, the formation of a fluid bed in which the shaped bodies circulate elliptically in a particularly uniform manner, which is associated with a rise in the product quality. This elliptical circulating motion can be converted to a fluid bed by means of a second movement component, as can be generated, for example, either by means of guide elements mounted on the annular slots or of a further vertical process gas component, which enables toroidal circulation of the shaped bodies.

In order to ensure particularly uniform spraying of the shaped bodies, for example with noble metal solutions, in a further preferred embodiment, an annular gap nozzle whose opening is configured such that the nozzle can be used to spray a spray cloud whose mirror plane runs parallel to the bottom plane may be arranged centrally in the bottom.

In addition, it may be preferred that exit orifices for support gas are provided between the opening of the annular gap nozzle and the bottom below, in order to bring about a support cushion on the underside of the spray cloud. The air cushion on the bottom side keeps the bottom surface free from sprayed solution, i.e. all of the solution sprayed is introduced into the fluid bed of the shaped bodies, such that no spray losses occur, which is of significance especially with regard to expensive noble metal compounds or enzymes for reasons of cost.

In a further preferred embodiment of the inventive use, in the device, the support gas is provided by the annular gap nozzle itself and/or by process gas. These measures permit very variable configurations of the provision of the support gas. On the annular gap nozzle, it is possible even for exit orifices to be provided, through which a portion of the spray gas exits, in order to contribute to the formation of the support gas. Additionally or alternatively, portions of the process gas which flows through the bottom are conducted in the direction of the underside of the spray cloud and hence contribute to the formation of the support gas.

In a further embodiment of the invention, the annular gap nozzle has a conical head and the opening runs along a circular cone section face. This ensures that the cone supplies shaped bodies moving vertically from the top downward in a uniform and controlled manner to the spray cloud, which is sprayed by the circular spray gap in the lower end of the cone.

In a further embodiment of the use, a frustoconical wall is provided in the region between the opening and bottom below, and preferably has passage orifices for support gas. This measure has the advantage that the aforementioned harmonic deflecting motion at the cone is maintained by the continuation above the frustocone and support gas can exit through the passage orifices in this region and ensures the corresponding support on the underside of the spray cloud.

In a further embodiment of the use, a annular slot is formed between the underside of the frustoconical wall for the passage of process gas. This measure has the advantage that the transition of the shaped bodies to the air cushion of the bottom can be controlled particularly efficiently and can be carried out in a controlled manner beginning immediately in the region below the nozzle.

In order to be able to introduce the spray cloud into the fluid bed at the desired height, it is preferred that the position of the opening of the nozzle is height-adjustable.

In a further embodiment of the inventive use, guide elements which impart a circumferential flow component to the process gas passing through are disposed between the annular guide plates.

WORKING EXAMPLES

The working examples which follow serve to illustrate the invention.

Example 1

225 g of spherical shaped catalyst support bodies, formed from an acid-treated calcined bentonite as a natural sheet silicate, from SÜD-Chemie AG (Munich, Germany), having the trade name "KA-0" and the characteristics listed in Table 1:

TABLE 1

| Geometric shape | Sphere |
|---|---|
| Diameter | 5 mm |
| Moisture content | <2.0% by mass |
| Pressure resistance | >40 N |
| Bulk density | 550 g l$^{-1}$ |
| Water absorption capacity | 67% |
| Specif. surface area (BET) | 104 m$^2$ g$^{-1}$ |
| SiO$_2$ content | 95.8% by mass |
| Al$_2$O$_3$ content | 1.5% by mass |
| Fe$_2$O$_3$ content | 0.3% by mass |
| TiO$_2$ content | (sum) <1.5% by mass |
| MgO content | |
| CaO content | |
| K$_2$O content | |
| Na$_2$O content | |
| Ignition loss 1000° C. | <0.3% by mass |
| Acidity | 50 µeq/g |
| BJH pore volume N$_2$ | 0.4 cm$^3$ g$^{-1}$ | were charged into a fluid bed device from Innojet Technologies (Lörrach, Germany) with the trade name Innojet® Aircoater, and converted to a fluid bed state by means of compressed air (6 bar) heated to 100° C., in which the shaped bodies circulated toroidally, i.e. moved on a vertically aligned ellipsoidal circular path and a horizontal circular path aligned at right angles thereto.

Once the shaped bodies had been heated to a temperature of approx. 75° C., 300 ml of an aqueous mixed noble metal solution containing 7.5 g of commercial Na$_2$PdCl$_4$ (sodium tetrachloropalladate) and 4.6 g of commercial NaAuCl$_4$ (sodium tetrachloroaurate) were sprayed onto the fluid bed of the shaped bodies over a period of 40 min.

After the catalyst supports had been impregnated with the mixed noble metal solution, a 0.05 molar NaOH solution was sprayed onto the fluid bed of the shaped bodies at a temperature of 80° C. over a period of 30 min. In the course of this, the NaOH is deposited predominantly within the shell and fixes the Pd and Au metal components, without the support being exposed to excessively great NaOH concentrations.

After the action of NaOH, the supports were washed copiously with water in the fluid bed device, in order to very substantially free the supports of alkali metal and chloride introduced into the supports via the noble metal compounds and NaOH.

After the washing, the shaped bodies were dried in the fluid bed device by movement in hot process air (100° C.).

After the shaped bodies had been dried, they were reduced with a gas mixture of ethylene (5% by volume) in nitrogen at a temperature of about 150° C. in the fluid bed device to give a Pd/Au shell catalyst.

The resulting shell catalyst contained approx. 1.2% by mass of Pd and had an Au/Pd atomic ratio of approx. 0.5, a shell thickness of approx. 160 µm and a hardness of 38 N.

The noble metal concentration of the Pd/Au shell catalyst thus produced deviated over a range of 90% of the shell thickness, the region being spaced apart from the outer and inner shell limit in each case by 5% of the shell thickness, from the mean noble metal concentration of this region by not more than +/−10%.

The noble metal distribution was determined on an LEO 430VP scanning electron microscope, equipped with an energy-dispersive spectrometer from Bruker AXS. To measure the noble metal concentration over the shell thickness, a catalyst sphere was cut through, adhesive-bonded to an aluminum sample holder and then subjected to vapor deposition of carbon. The detector used was a nitrogen-free silicon drift chamber detector (XFlash® 410) with an energy resolution of 125 eV for the manganese K$_{alpha}$ line.

The following parameters were used for the analysis:
Scan resolution: 500 points
Separation of the measurement points: 1.8 µm
Magnification: 200-fold
Jet voltage 20 kV
Jet current 20 nA
Input pulse rate: 50000 pulse/s
Measurement time for line scan: 200 s For other elements (see subsequent examples), the corresponding available lines are employed for the measurement.

The shell thickness of 100 spheres of the shell catalyst charge produced as described above was measured. The ratio of the standard deviation of the shell thicknesses of the shell catalysts of the charge to the mean of the shell thicknesses of the shell catalysts of the charge was less than 10%.

Example 2

Shell catalysts were produced analogously to Example 1, with the exception that, instead of the Pd/Au solution, a solution containing 25 mmol of CuCl$_2$ was used and that there was no fixing and no washing.

The resulting shell catalyst contained approx. 0.7% by mass of Cu and had a shell thickness of approx. 136 µm.

The metal concentration of the shell catalyst thus produced deviated over a region of 90% of the shell thickness, the region being spaced apart from the outer and inner shell limit in each case by 5% of the shell thickness, from the mean metal concentration of this region by not more than +/−20% (measurement as in Example 1).

The shell thickness of 100 spheres of the shell catalyst charge produced as described above was measured. The ratio of the standard deviation of the shell thicknesses of the shell catalysts of the charge to the mean of the shell thicknesses of the shell catalysts of the charge was less than 10%.

Example 3

Shell catalysts were produced analogously to Example 1, with the exception that, instead of the Pd/Au solution, a solution containing 26 mmol of Na$_2$PdCl$_4$ was used and that there was neither any fixing nor any washing.

The resulting shell catalyst contained approx. 1.0% by mass of Pd and had a shell thickness of approx. 93 µm.

The metal concentration of the shell catalyst thus produced deviated over a region of 90% of the shell thickness, the region being spaced apart from the outer and inner shell limit in each case by 5% of the shell thickness, from the mean metal concentration of this region by not more than +/−20% (measurement as in Example 1).

The shell thickness of 100 spheres of the shell catalyst charge produced as described above was measured. The ratio of the standard deviation of the shell thicknesses of the shell catalysts of the charge to the mean of the shell thicknesses of the shell catalysts of the charge was less than 10%.

Example 4

Shell catalysts were produced analogously to Example 1, with the exception that, instead of the Pd/Au solution, a solution containing 26 mmol of Pd(NH$_3$)$_4$(OH)$_2$ was used and that there was neither any fixing nor any washing.

The resulting shell catalyst contained approx. 1.0% by mass of Pd and had a shell thickness of approx. 71 μm.

The metal concentration of the shell catalyst thus produced deviated over a region of 90% of the shell thickness, the region being spaced apart from the outer and inner shell limit in each case by 5% of the shell thickness, from the mean metal concentration of this region by not more than +/−20% (measurement as in Example 1).

The shell thickness of 100 spheres of the shell catalyst charge produced as described above was measured. The ratio of the standard deviation of the shell thicknesses of the shell catalysts of the charge to the mean of the shell thicknesses of the shell catalysts of the charge was less than 10%.

Comparative Example 1

65.02 g of shaped catalyst support bodies from Süd-Chemie AG (Munich, Germany) with the trade name "KA-160" and with the characteristic data reported in Table 2 are impregnated by the pore filling method (incipient wetness method), in which a support is impregnated with a volume of solution corresponding to its pore volume, with 39.1 ml of an aqueous solution containing 1.568 g of $Na_2PdCl_4$ and 0.367 g of $HAuCl_4$. After the impregnation, 89.17 g of 0.35 molar NaOH solution are added to the shaped catalyst support bodies and left to stand at room temperature overnight for 22 hours. After the fixing solution has been decanted, the catalyst precursor thus produced is reduced with 73.68 g of a 10% $NaH_2PO_2$ solution (Fluka) for 2 hours. After the reduction solution has been discharged, the catalysts are washed with dist. water to remove Cl residues with constant exchange of the water (flow=140 rpm) at room temperature for 8 hours. The final value of the conductivity of the wash solution is 1.2 μS.

Thereafter, the catalyst is dried in the fluid bed at 90° C. for 50 min. The dried spheres are loaded with a mixture of 27.29 g of 2 molar KOAc solution and 18.55 g of $H_2O$ and left to stand at room temperature for 1 hour. Finally, they are dried at 90° C. in the fluid bed for 40 min.

The theoretical metal loading is 0.8% by weight of Pd and 0.3% by weight of Au; the values determined experimentally by elemental analysis by means of ICP (Inductively Coupled Plasma) were 0.78% by weight of Pd and 0.26% by weight of Au.

The shell thickness was 280 μm.

TABLE 2

| Geometric shape | Sphere |
|---|---|
| Diameter | 5 mm |
| Moisture content | <2.0% by mass |
| Pressure resistance | >60 N |
| Bulk density | 554 g l$^{-1}$ |
| Water absorption capacity | 62% |
| Specif. surface area (BET) | 158 m$^2$ g$^{-1}$ |
| $SiO_2$ content | 93.2% by mass |
| $Al_2O_3$ content | 2.2% by mass |
| $Fe_2O_3$ content | 0.35% by mass |
| $TiO_2$ content | (sum) <1.5% by mass |
| MgO content | |
| CaO content | |
| $K_2O$ content | |
| $Na_2O$ content | |
| Ignition loss 1000° C. | <0.3% by mass |
| Acidity | 53 μeq/g |
| BJH pore volume $N_2$ | 0.38 cm$^3$ g$^{-1}$ |

Example 5

65.02 g of spherical shaped catalyst support bodies, formed from an acid-treated calcined bentonite as a natural sheet silicate, from SÜD-Chemie AG (Munich, Germany) having the trade name "KA-160" and the characteristics listed in Table 2 were charged into a fluid bed device from Innojet Technologies (Lörrach, Germany) with the trade name Innojet® Aircoater and converted to a fluid bed state by means of compressed air (6 bar) heated to 90° C., in which the shaped bodies circulated toroidally.

300 ml of an aqueous solution containing 1.568 g of $Na_2PdCl_4$ and 0.367 g of $HAuCl_4$ were sprayed onto the fluid bed of the shaped bodies over a period of 40 min.

After the impregnation, 89.17 g of 0.35 molar NaOH solution are added to the shaped catalyst support bodies and left to stand at room temperature overnight for 22 hours. After the fixing solution has been decanted, the catalyst precursor thus produced is reduced with 73.68 g of a 10% $NaH_2PO_2$ solution (Fluka) for 2 hours. After the reduction solution has been discharged, the catalysts are washed with dist. water to remove Cl residues with constant exchange of the water (flow=140 rpm) at room temperature for 8 hours. The final value of the conductivity of the wash solution is 1.2 μS.

Thereafter, the catalyst is dried in the fluid bed at 90° C. for 50 min. The dried spheres are loaded with a mixture of 27.29 g of 2 molar KOAc solution and 18.55 g of $H_2O$, and left to stand at room temperature for 1 hour. Finally, they are dried at 90° C. in the fluid bed for 40 min.

The theoretical metal loading is 0.8% by weight of Pd and 0.3% by weight of Au; the values determined experimentally by means of ICP were 0.75% by weight of Pd and 0.25% by weight of Au.

The shell thickness was 205 μm.

Example 6

Reactor Test 6 ml of a bed of catalyst spheres according to Example 5 and Comparative example 1 were each exposed in a fixed bed tubular reactor at a temperature of 150° C. at 10 bar to a feed gas stream of 550 ml (STP)/min composed of 15% HOAc, 6% 39% $C_2H_4$ in $N_2$, and the reactor effluent was analyzed by means of gas chromatography.

The selectivity (of ethylene for VAM) is calculated by the formula $S(C_2H_4)$=mol VAM/(mol VAM+mol $CO_2$/2). The space-time yield is found as g of VAM/l of catalyst/h. The oxygen conversion is calculated by (mol $O_2$ in−mol $O_2$ out)/mol $O_2$ in.

The catalyst produced by means of the method according to the invention in Example 5 exhibits a selectivity $S(C_2H_4)$ of 92.3% and a space-time yield (determined by gas chromatography) of 654 g of VAM/l of catalyst/h at an oxygen conversion of 38.7%.

The catalyst according to Comparative Example 1 exhibited a selectivity $S(C_2H_4)$ of 91.0% and a space-time yield (determined by gas chromatography) of 576 g of VAM/l of catalyst/h at an oxygen conversion of 36.1%.

The catalyst produced by means of the method according to the invention in Example 5 exhibits both a higher selectivity and activity in the VAM synthesis compared to a catalyst produced by a prior art method in Comparative Example 1.

BRIEF DESCRIPTION OF THE DRAWINGS

The description which follows of a preferred device for performing the method according to the invention and the description of the movement paths of shaped catalyst support bodies, in combination with the drawing, serves to illustrate the invention. The drawings show:

FIG. 1A a vertical section view of a preferred device for performing the method according to the invention;

FIG. 1B an enlargement of the area framed in FIG. 1A and marked with reference numeral 1B;

FIG. 2A a perspective section view of the preferred device, in which the movement paths of two elliptically circulating shaped catalyst support bodies are shown schematically;

FIG. 2B a plan view of the preferred device and the movement paths according to FIG. 2A;

DETAILED DESCRIPTION OF THE PREFERRED EMBODIMENTS

Figure 3A:
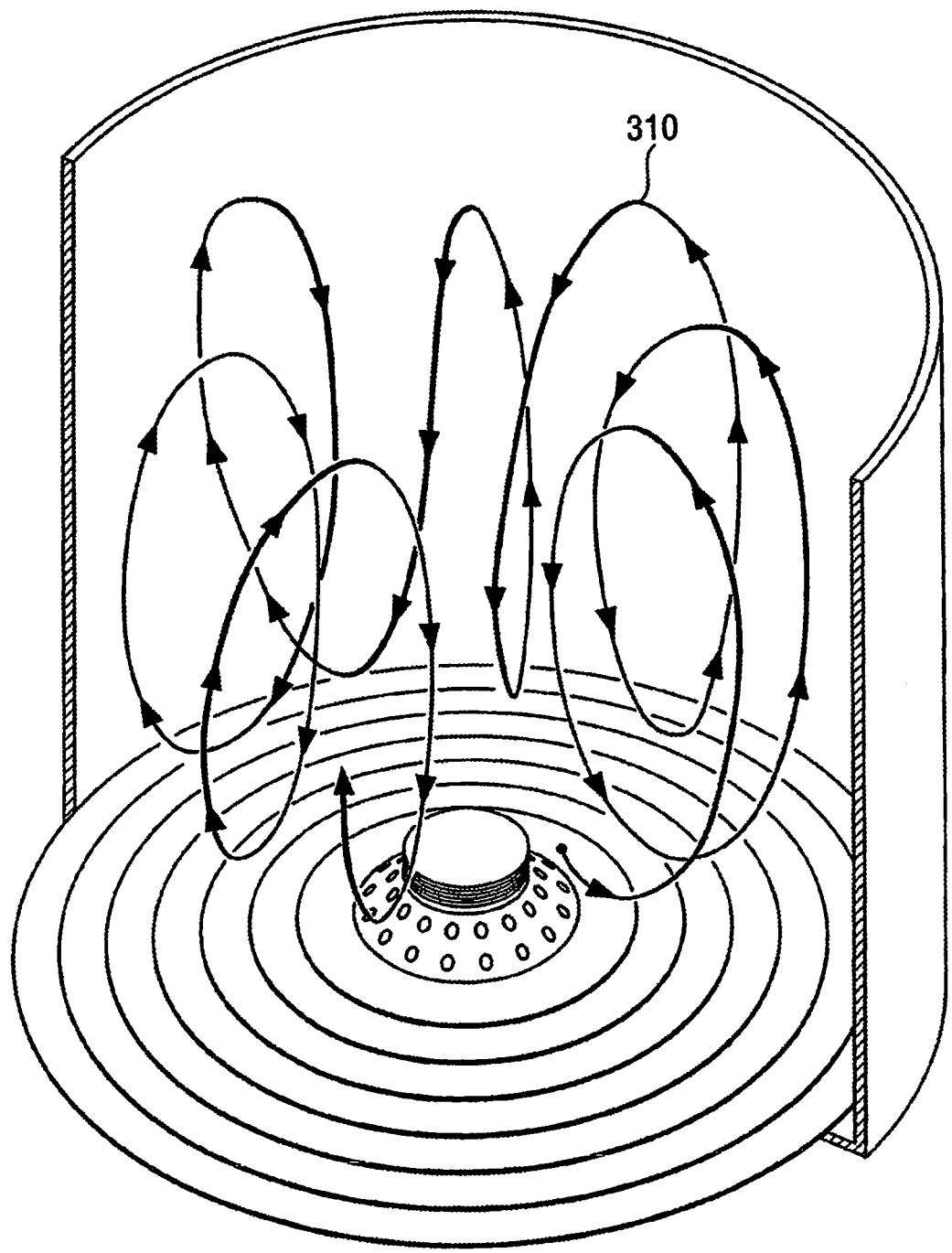
FIG. 3A a perspective section view of the preferred device, in which the movement path of a toroidally circulating shaped catalyst support body is shown schematically.

FIG. 1A shows an device given the reference numeral 10 as a whole for performing the method according to the invention.

The device 10 has a vessel 20 with an upright cylindrical side wall 18 which encloses a process chamber 15.

The process chamber 15 has a bottom 16 under which is disposed an inflow chamber 30.

The bottom 16 is composed of a total of seven annular ring plates as guide plates, laid one on top of another. The seven ring plates are placed one on top of another such that an outermost ring plate 25 forms a lowermost ring plate, on which the further six inner ring plates are then placed, each of which lying below and some of which overlapping.

For the sake of clarity, only some of the total of seven ring plates are provided with reference numerals, for example the two ring plates 26 and 27 lying one on top of the other. By virtue of this superposition and spacing, a annular slot 28 is formed in each case between two ring plates, through which process air 40 can pass through the bottom 16 as process gas with a predominantly horizontally directed movement component.

In the central uppermost inner ring plate 29, an annular gap nozzle 50 is inserted from below in the central orifice thereof. The annular gap nozzle 50 has an opening 55 which has a total of three opening gaps 52, 53 and 54. All three opening gaps 52, 53 and 54 are aligned such that they spray out approximately parallel to the bottom 16, i.e. approximately horizontally with a coverage angle of 360°. Spray air is sprayed out as spray gas through the upper gap 52 and the lower gap 54, and the solution to be sprayed through the middle gap 53.

The annular gap nozzle 50 has a rod-shape body 56 which continues downward and contains the appropriate channels and feed lines, which are known per se and are therefore not shown in the drawing. The annular gap nozzle 50 may, for example, be configured with a so-called rotative ring gap, in which walls of the channel through which the solution is sprayed turn relatively to one another, in order to prevent blockages of the nozzle, such that it is possible to spray uniformly out of the gap 53 over the coverage angle of 360°.

The annular gap nozzle 50 has a conical head 57 above the opening gap 52.

In the region below the opening gap 54, a frustoconical wall 58 is present, which has numerous orifices 59. As is evident from FIG. 1B, the underside of the frustoconical wall 58 rests on the innermost ring plate 29 in such a way that, between the underside of the frustoconical wall 58 and the ring plate 29 which lies below it and overlaps partly with it, a slot 60 is formed, through which process air 40 can pass.

The outer ring 25 is spaced apart from the wall 18, such that process air 40 can enter the process chamber 15 with a predominantly vertical component in the direction of the arrow given the reference numeral 61, and thus imparts a comparatively great component directed upward to the process air 40 entering the process chamber 15 through the slots 28.

The right-hand half of FIG. 1A shows what conditions form in the device 10 in a state after runin.

A spray cloud 70 emerges from the opening gap 53, and the horizontal mirror plane thereof runs approximately parallel to the bottom plane. As a result of the air which passes through the orifices 59 in the frustoconical wall 58, which may, for example, be process air 40, a support air flow 72 forms on the underside of the spray cloud 70. As a result of the process air 40 passing through the numerous slots 28, a radial flow in the direction of the wall 18 forms, by which the process air 40 is deflected upward, as shown by the arrow given the reference numeral 74. The deflected process air 40 deflects the shaped bodies upward in the region of the wall 18. The process air 40 and the shaped catalyst support bodies to be treated are then separated from one another, the process air 40 being removed through outlets, while the shaped bodies move radially according to the arrows 75 inward in the direction of the conical head 57 of the annular gap nozzle 50 vertically downward. The shaped bodies are deflected there, guided to the upper side of the spray cloud 70 and treated there with the medium sprayed. The sprayed shaped bodies then move again in the direction of the wall 18 while moving away from one another, since, after leaving the spray cloud 70 at the annular opening gap 53, a greater space in terms of area is available to the shaped bodies. In the region of the spray cloud 70, the shaped bodies to be treated meet liquid particles and are moved away from one another remaining in the direction of movement in the direction of the wall 18 while being treated very uniformly and harmonically with the process air 40 and dried at the same time.

FIG. 2A shows two possible movement paths of two elliptically circulating shaped catalyst support bodies by means of the curve profiles given reference numerals 210 and 220. The elliptical movement path 210 has—compared to an ideal elliptical path—relatively large variations in the size of the main and secondary axis. The elliptical movement path 220, in contrast, has a relatively small change in the size of the main and secondary axis and describes virtually an ideal elliptical path without any circumferential (horizontal) movement component, as can be discerned from FIG. 2B.

Figure 3B:
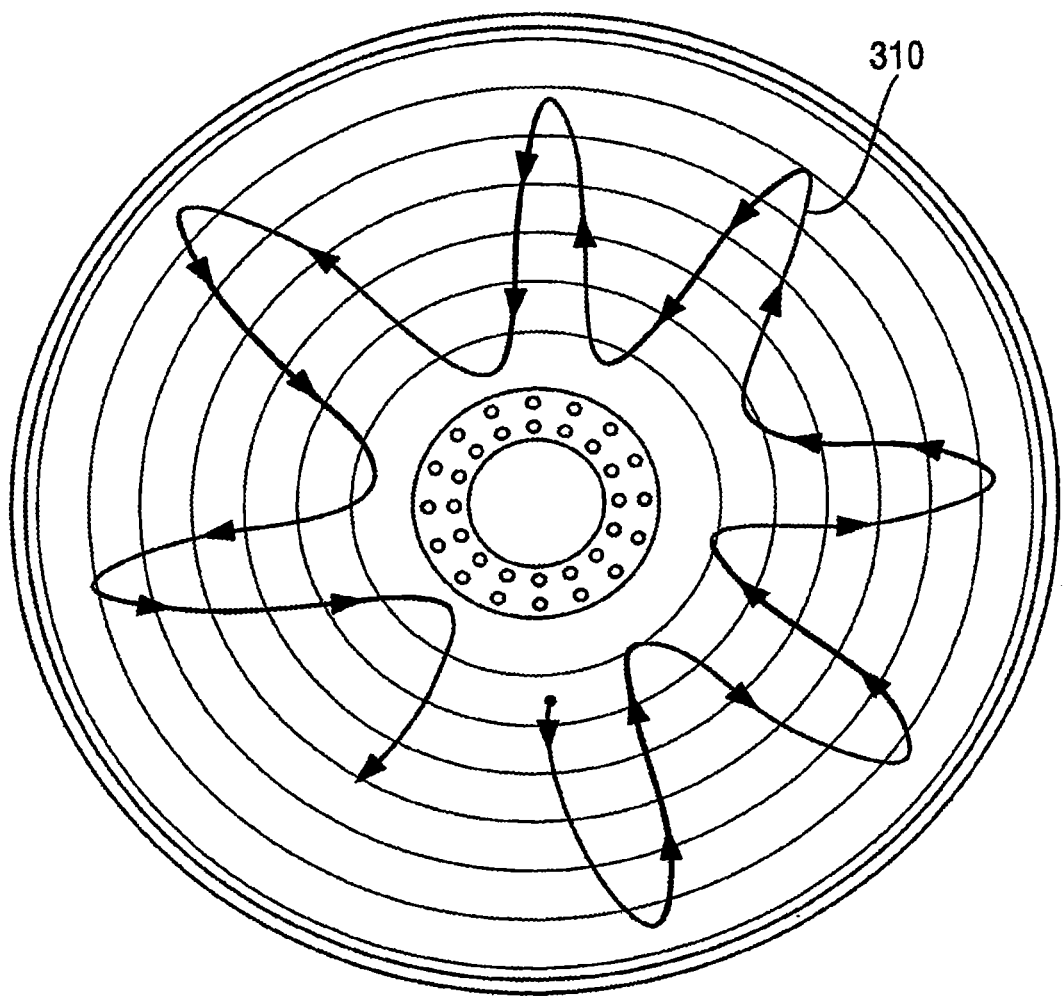
FIG. 3B a plan view of the preferred device and the movement path according to FIG. 3A.

FIG. 3A shows a possible movement path of a toroidally circulating shaped catalyst support body by means of the curve profile given reference numeral 310. The toroidally circulating movement path 310 describes a section of the surface of a virtually uniform torus, whose vertical section is elliptical and whose horizontal section is annular. FIG. 3B shows the movement path 310 in plan view.

The invention claimed is:

1. A method for producing a shell catalyst which comprises a porous catalyst support shaped body having an outer shell within which at least one catalytically active species is present, the method being performed using a device which is designed to generate, by means of a process gas, a fluid bed of catalyst support shaped bodies in which the catalyst support shaped bodies circulate elliptically or toroidally, comprising the steps of:

a) charging the device with catalyst support shaped bodies and generating a catalyst support shaped body fluid bed by means of a process gas, the shaped catalyst support bodies circulating elliptically or toroidally in the fluid bed;

b) impregnating an outer shell of the catalyst support shaped body with a catalytically active species or precursor thereof by spraying the catalyst support shaped bodies circulating elliptically or toroidally in the fluid bed with a solution comprising a catalytically active species or a precursor thereof;

c) drying the shaped catalyst support bodies sprayed with the solution, wherein the device comprises a process chamber with a bottom and a side wall, wherein the process gas being fed with a horizontal movement component directed radially outwards into the process chamber through the bottom of the process chamber, the bottom being constructed of several overlapping annular guide plates laid one over another, between which annular slots are formed, for generating the fluid bed.

2. Method according to claim 1, characterized in that the method further comprises a step of converting the precursor to a catalytically active species.

3. Method according to claim 1, characterized in that the process gas fed into the process chamber is subjected to a circumferential flow component.

4. Method according to claim 3, characterized in that the process gas fed into the process chamber is subjected to the circumferential flow component by means of guide elements which are arranged between the annular guide plates.

5. Method according to claim 1, characterized in that the process gas fed into the process chamber is subjected to the circumferential flow component by feeding additional process gas, with a movement component directed diagonally upwards, through the bottom of the process chamber into the process chamber.

6. Method according to claim 1, characterized in that the spraying of the catalyst support shaped bodies circulating elliptically or toroidally within the fluid bed is carried out by means of an annular gap nozzle which atomizes a spray cloud which runs parallel to the plane of the bottom.

7. Method according to claim 6, characterized in that the annular gap nozzle is centrally arranged in the bottom and the mouth of the annular gap nozzle is embedded into the fluid bed.

8. Method according to claim 7, characterized in that a gas support cushion is produced on the underside of the spray cloud.

9. Method according to claim 1, characterized in that the catalyst support shaped body is formed based on a silicon oxide, aluminum oxide, zirconium oxide, titanium oxide, niobium oxide or of a natural sheet silicate.

10. Method according to claim 1, characterized in that the catalyst support shaped body has a surface area of less than/equal to 160 $m^2/g$.

11. Method according to claim 1, characterized in that the catalyst support shaped body has a surface area of from 160 to 40 $m^2/g$.

12. Method according to claim 1, characterized in that the catalyst support shaped body has a hardness of greater than/equal to 20 N.

13. Method according to claim 1, characterized in that the process gas is selected from the group consisting of air, oxygen, nitrogen and the noble gases.

14. Method according to claim 1, characterized in that the process gas is heated to a temperature of more than/equal to 40° C.

15. Method according to claim 1, characterized in that the process gas, before being fed into the process chamber, is enriched with the solvent of the solution within a range of from 10 to 50% of the saturation vapor pressure.

16. Method according to claim 1, characterized in that the solution comprises a biocatalyst as catalytically active species.

17. Method according to claim 1, characterized in that the solution comprises a metal compound of a metal selected from the group consisting of the transition metals as catalytically active species or as precursor thereof.

18. Method according to claim 17, characterized in that the solution comprises a noble metal as catalytically active species or as precursor thereof.

19. Method according to claim 17, characterized in that the solution comprises an Au compound as catalytically active species or as precursor thereof.

20. Method according to of claim 17, characterized in that the solution comprises an Ag compound as catalytically active species or as precursor thereof.

21. Method according to claim 17, characterized in that the solution comprises a Pt compound as catalytically active species or as precursor thereof.

22. Method according to claim 17, characterized in that the solution comprises, as the catalytically active species or as a precursor thereof, a Co, Ni and/or Cu compound.

23. Method according to claim 1, characterized in that the shaped catalyst support body, after being sprayed with the solution, is subjected to a fixing step for fixing the catalytically active species or the precursor thereof on the support.

24. Method according to claim 16, characterized in that the biocatalyst comprises an enzyme.

* * * * *